(12) United States Patent
Fayyaz

(10) Patent No.: US 12,108,961 B2
(45) Date of Patent: Oct. 8, 2024

(54) MULTI-PURPOSE MEDICAL DEVICE FOR STREAMLINED BILIARY AND OTHER INTERVENTIONS

(71) Applicant: Mohammad Fayyaz, East Amherst, NY (US)

(72) Inventor: Mohammad Fayyaz, East Amherst, NY (US)

( * ) Notice: Subject to any disclaimer, the term of this patent is extended or adjusted under 35 U.S.C. 154(b) by 0 days.

(21) Appl. No.: 18/480,394

(22) Filed: Oct. 3, 2023

(65) Prior Publication Data

US 2024/0058024 A1 Feb. 22, 2024

(51) Int. Cl.
*A61B 17/22* (2006.01)
*A61M 25/00* (2006.01)
*A61M 25/10* (2013.01)
*A61B 90/00* (2016.01)

(52) U.S. Cl.
CPC .......... *A61B 17/22032* (2013.01); *A61B 2017/22038* (2013.01); *A61B 2090/3933* (2016.02); *A61M 2025/0008* (2013.01); *A61M 2025/0036* (2013.01); *A61M 25/1011* (2013.01); *A61M 25/10182* (2013.11); *A61M 2025/1079* (2013.01)

(58) Field of Classification Search
CPC ........ A61B 17/22031; A61B 17/22032; A61B 2017/22034; A61B 2017/22035; A61B 2017/22038; A61B 2017/22051; A61B 2017/22054; A61B 2017/22072; A61B 18/04; A61B 17/3205; A61B 17/32056; A61B 2018/00535; A61B 2018/00553; A61B 2018/114; A61M 25/1011; A61M 2025/0036; A61M 2025/109; A61M 2210/1075

See application file for complete search history.

(56) References Cited

U.S. PATENT DOCUMENTS

| | | | | |
|---|---|---|---|---|
| 5,152,772 | A * | 10/1992 | Sewell, Jr. | A61B 17/320725 |
| | | | | 606/159 |
| 5,984,920 | A * | 11/1999 | Steinbach | A61B 18/14 |
| | | | | 606/45 |
| 2003/0229332 | A1* | 12/2003 | Intoccia | A61B 17/22 |
| | | | | 604/93.01 |
| 2009/0171369 | A1* | 7/2009 | Gayzik | A61M 25/1011 |
| | | | | 606/127 |
| 2016/0331454 | A1* | 11/2016 | Kobayashi | A61B 18/1492 |
| 2021/0315595 | A1* | 10/2021 | Crawford | A61M 25/1002 |

* cited by examiner

Primary Examiner — Martin T Ton

(57) ABSTRACT

The present invention relates to a methodology of, and an apparatus for, performing multiple interventions within the biliary tree without requiring multiple catheter exchanges. The device consists of a flexible elongate tube, introduced through an endoscope, having a proximal end towards the operator and a distal end directed towards a body lumen. The exposed part of an electrosurgical cutting wire near the distal end is used to cut the sphincter of Oddi. Two lumens extend from the proximal to the distal end, one configured to accept a guidewire, and the other to allow contrast injection. In some renderings, a single lumen may serve both functions. Another lumen extends from the proximal end to a dilator balloon housed distally on the catheter to further widen the biliary orifice. An additional lumen extends from the proximal end to an extractor balloon near the distal end of the catheter for stone extraction.

3 Claims, 18 Drawing Sheets

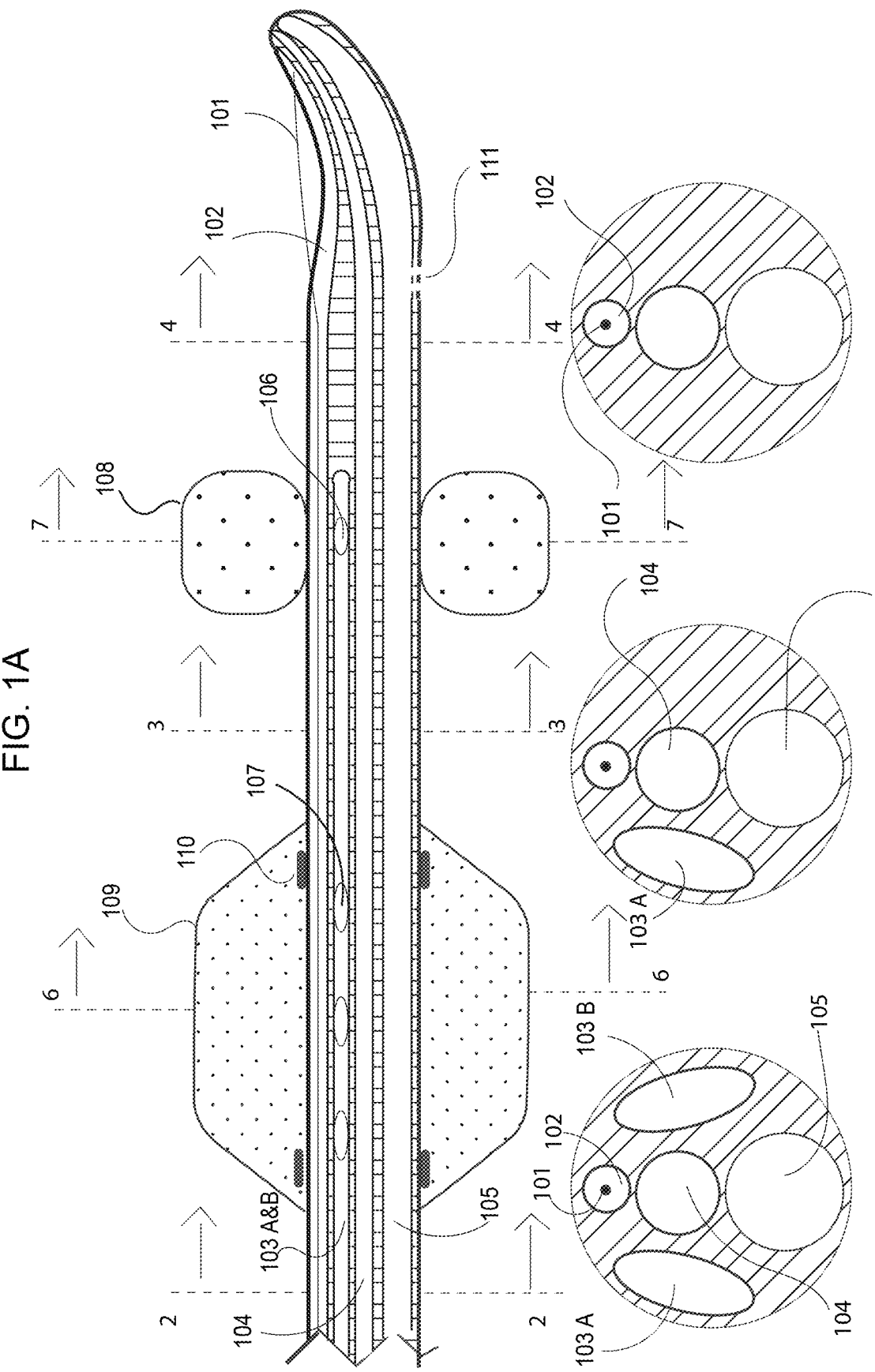

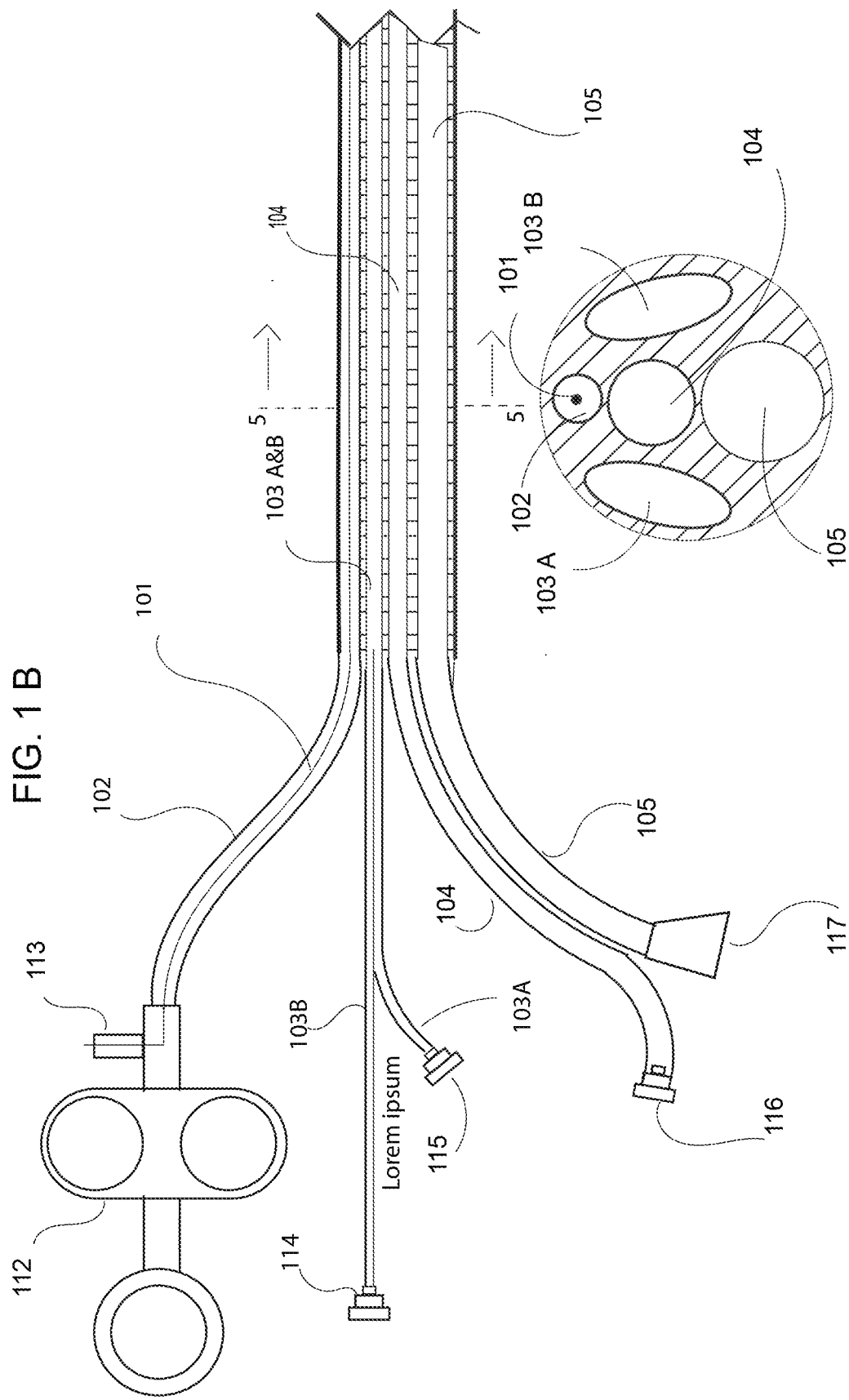

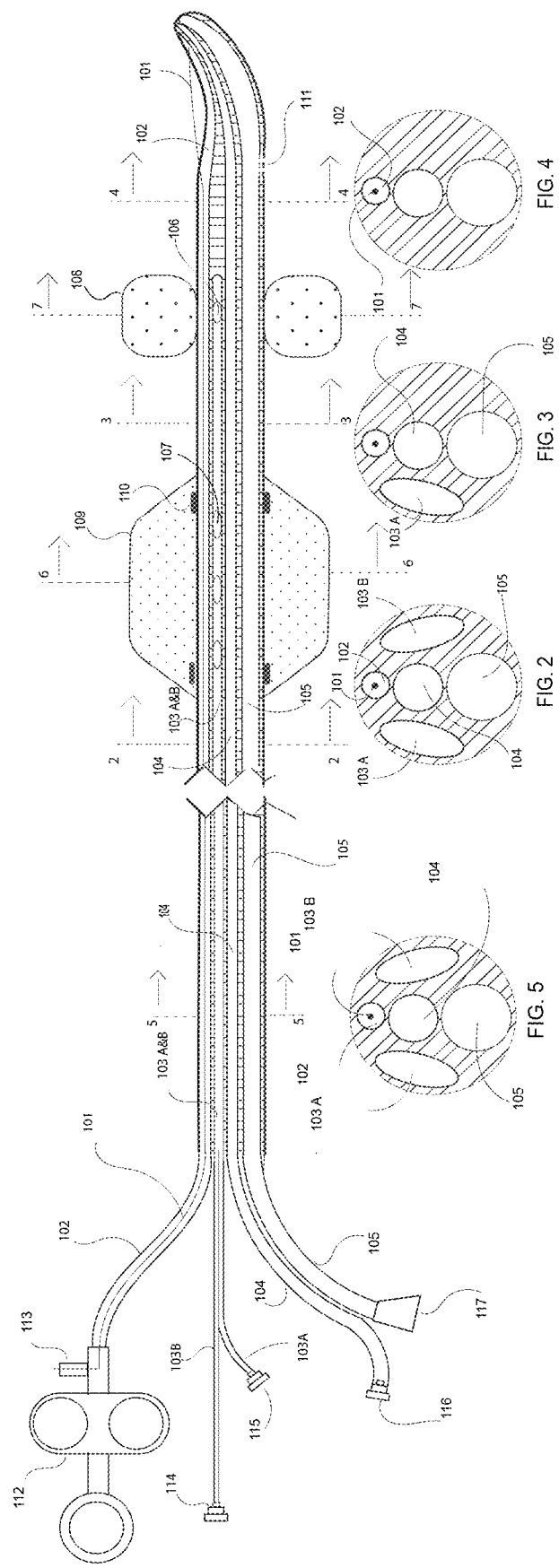

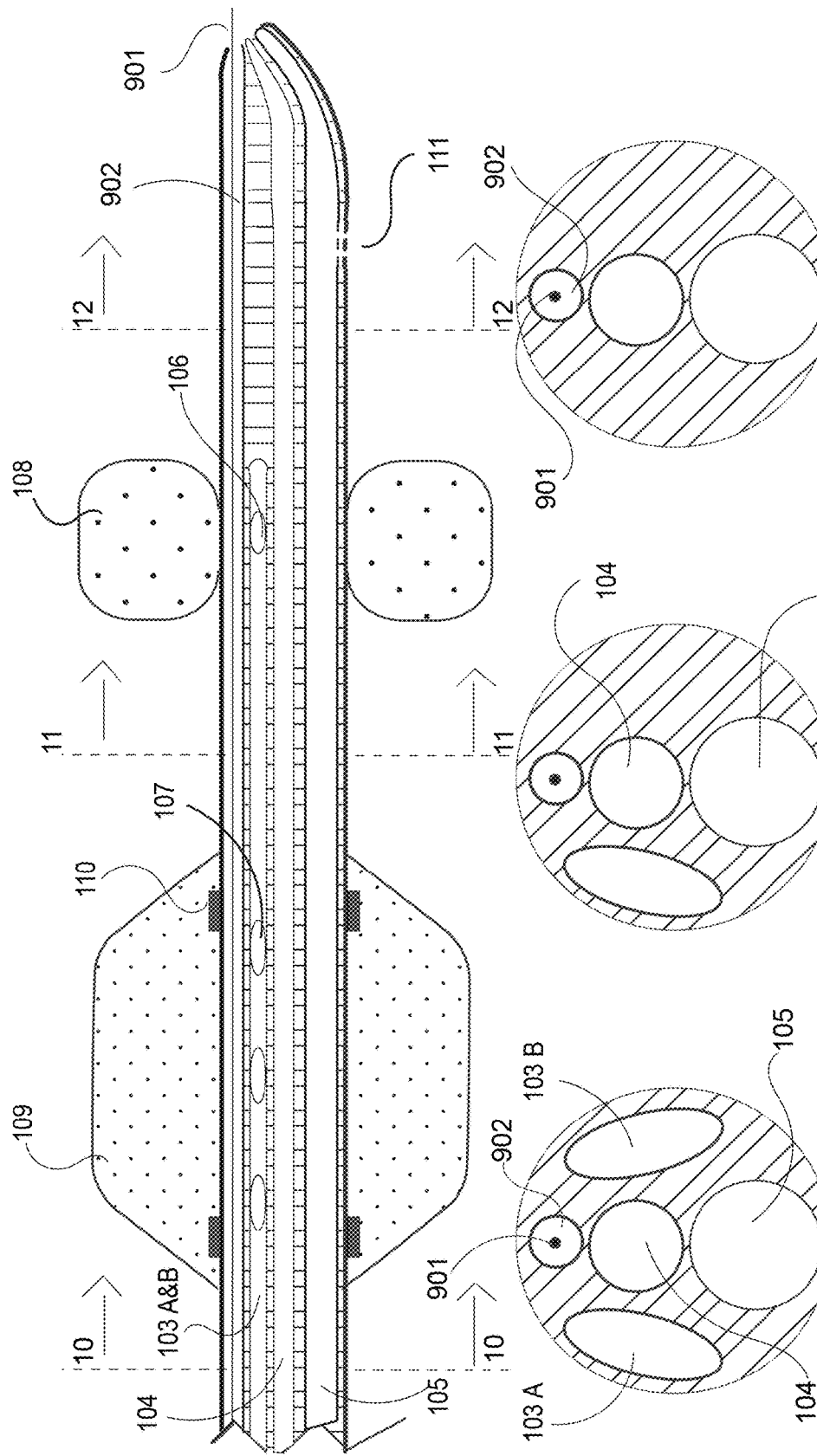

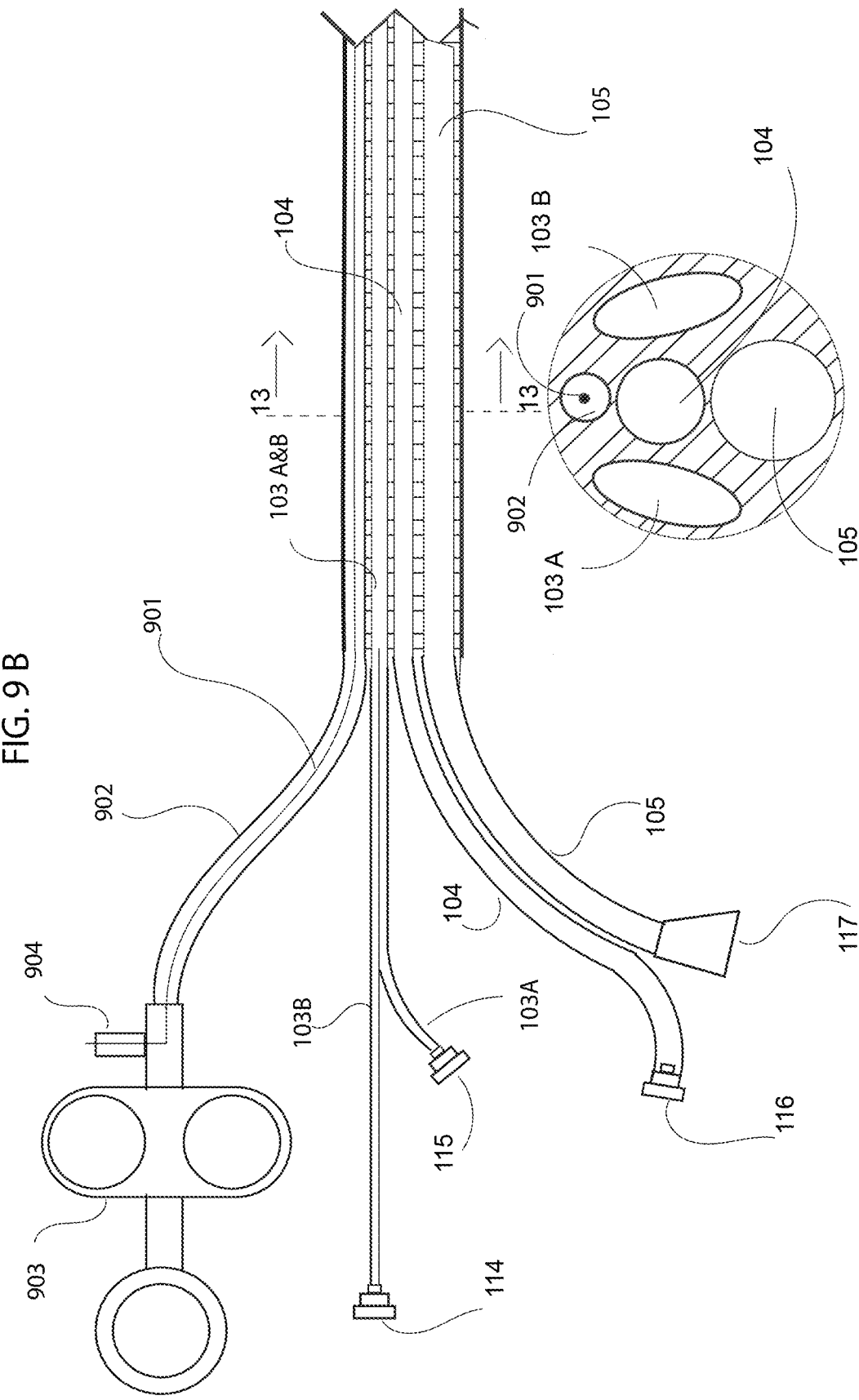

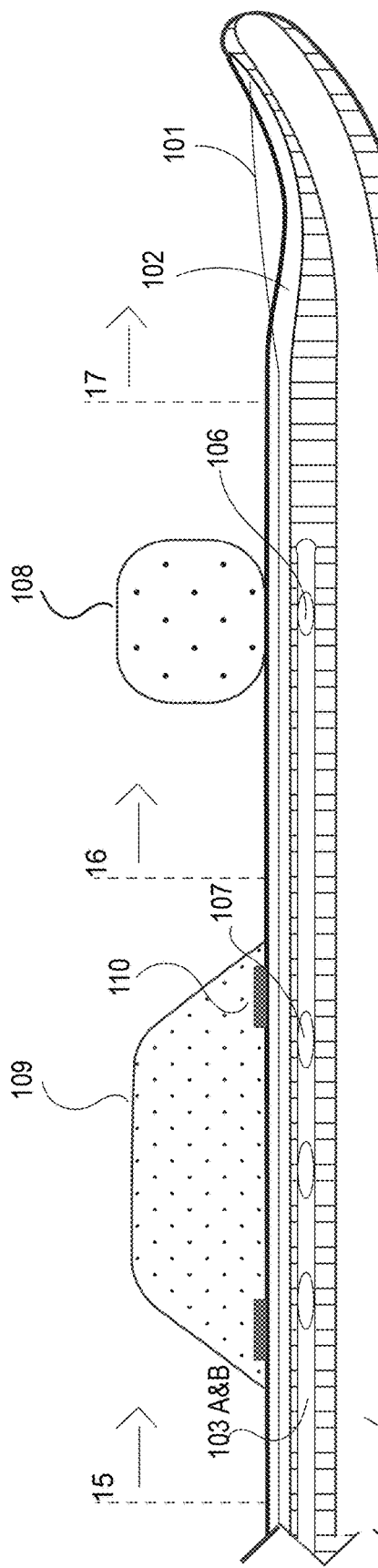
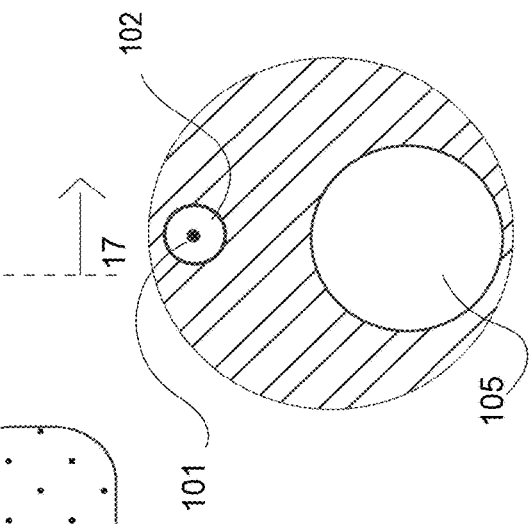
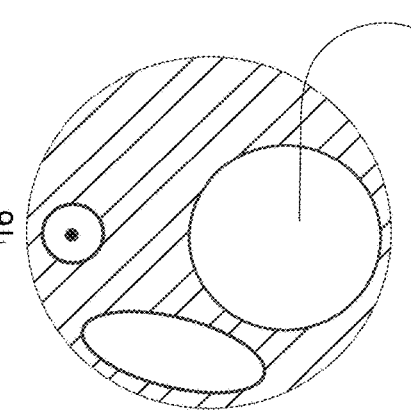
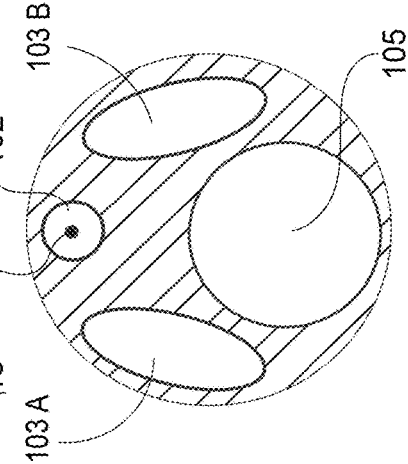

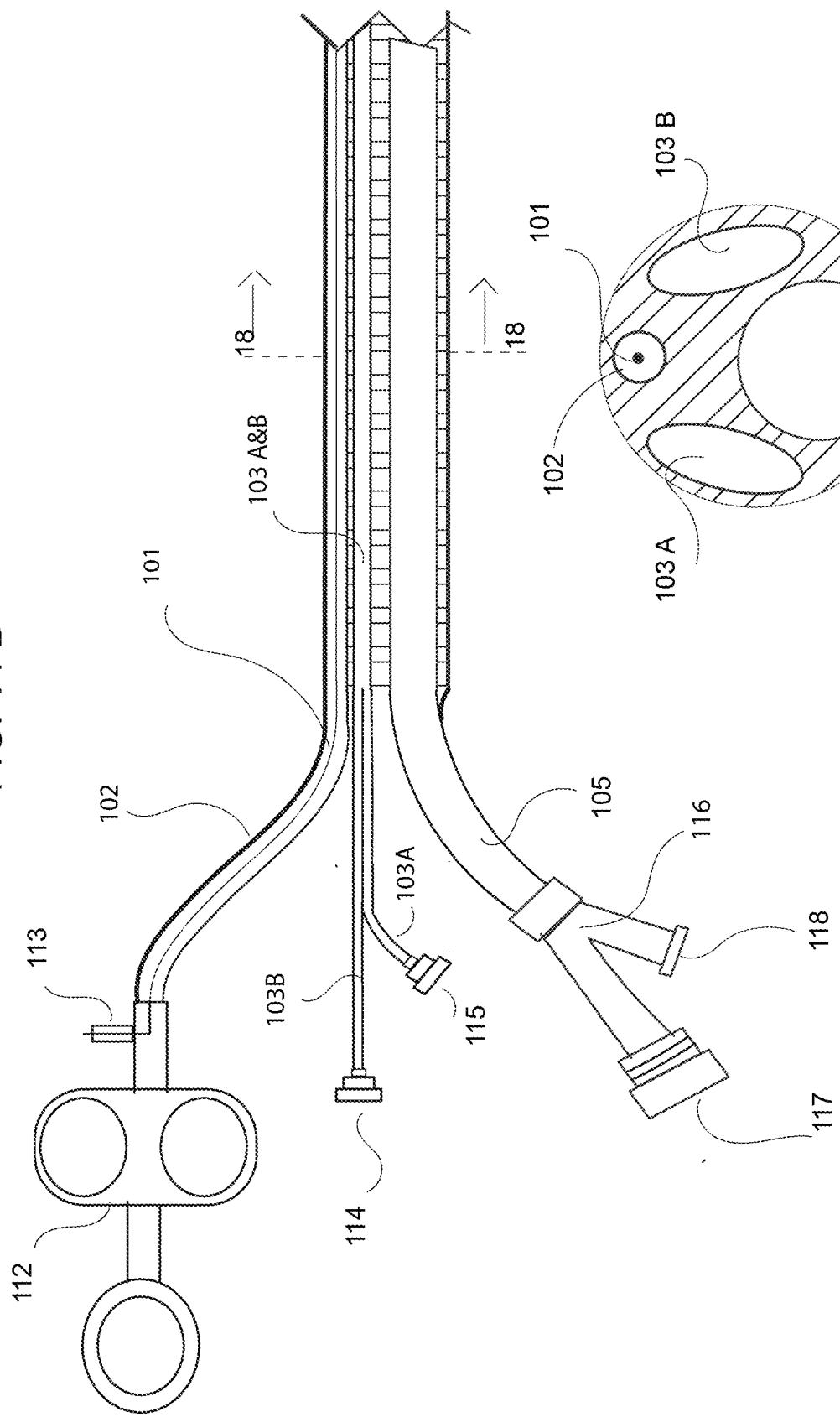

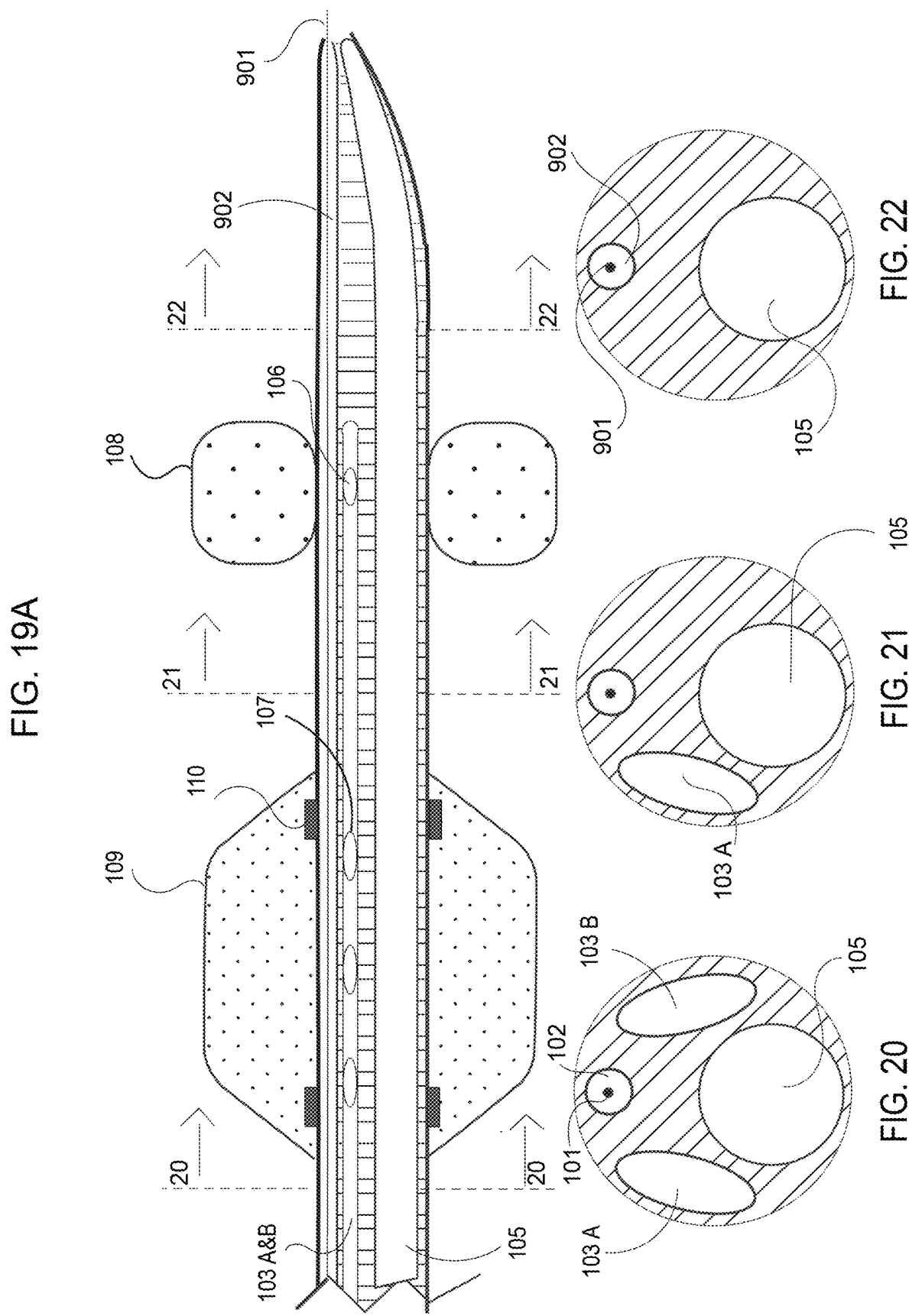

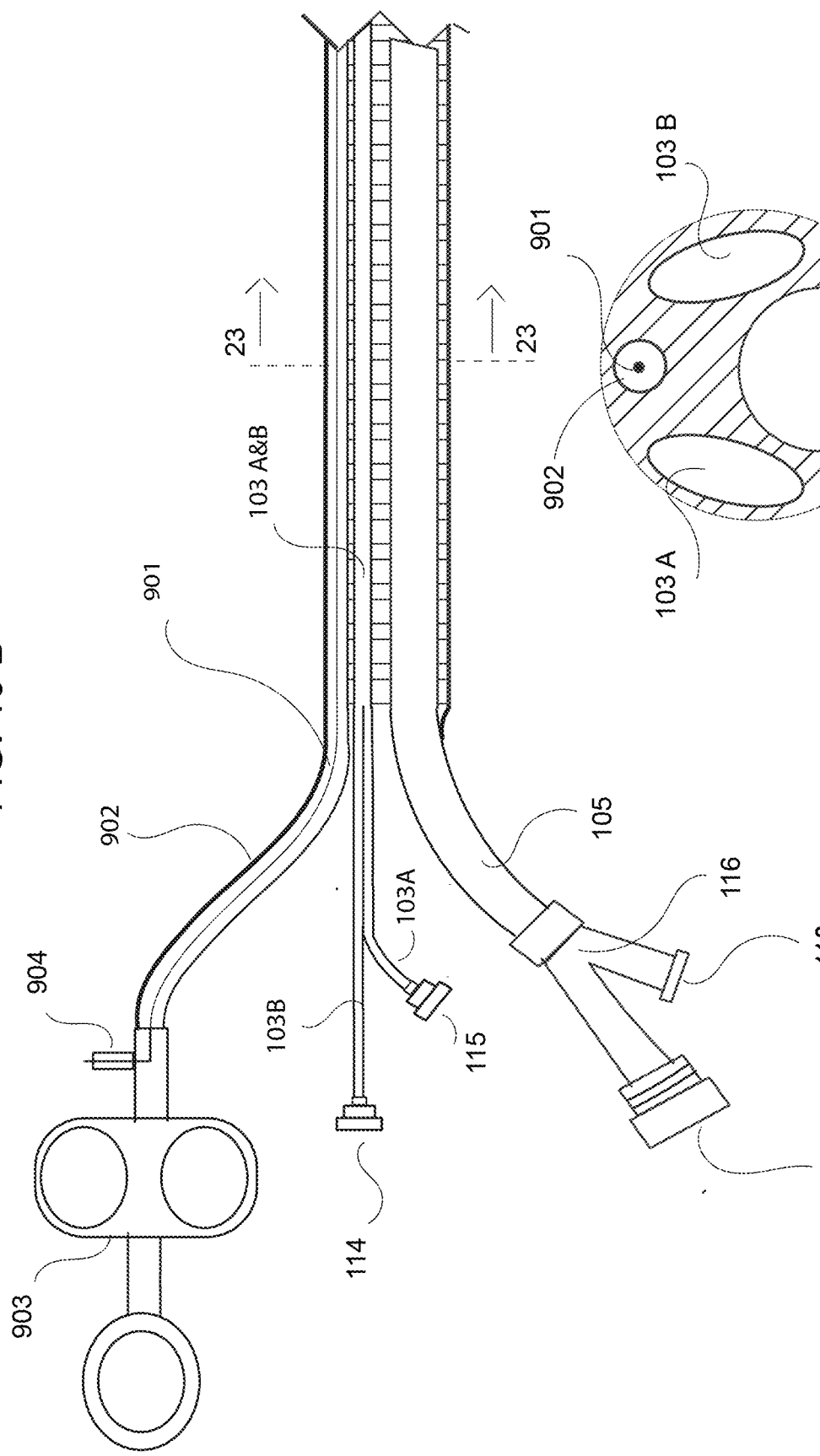

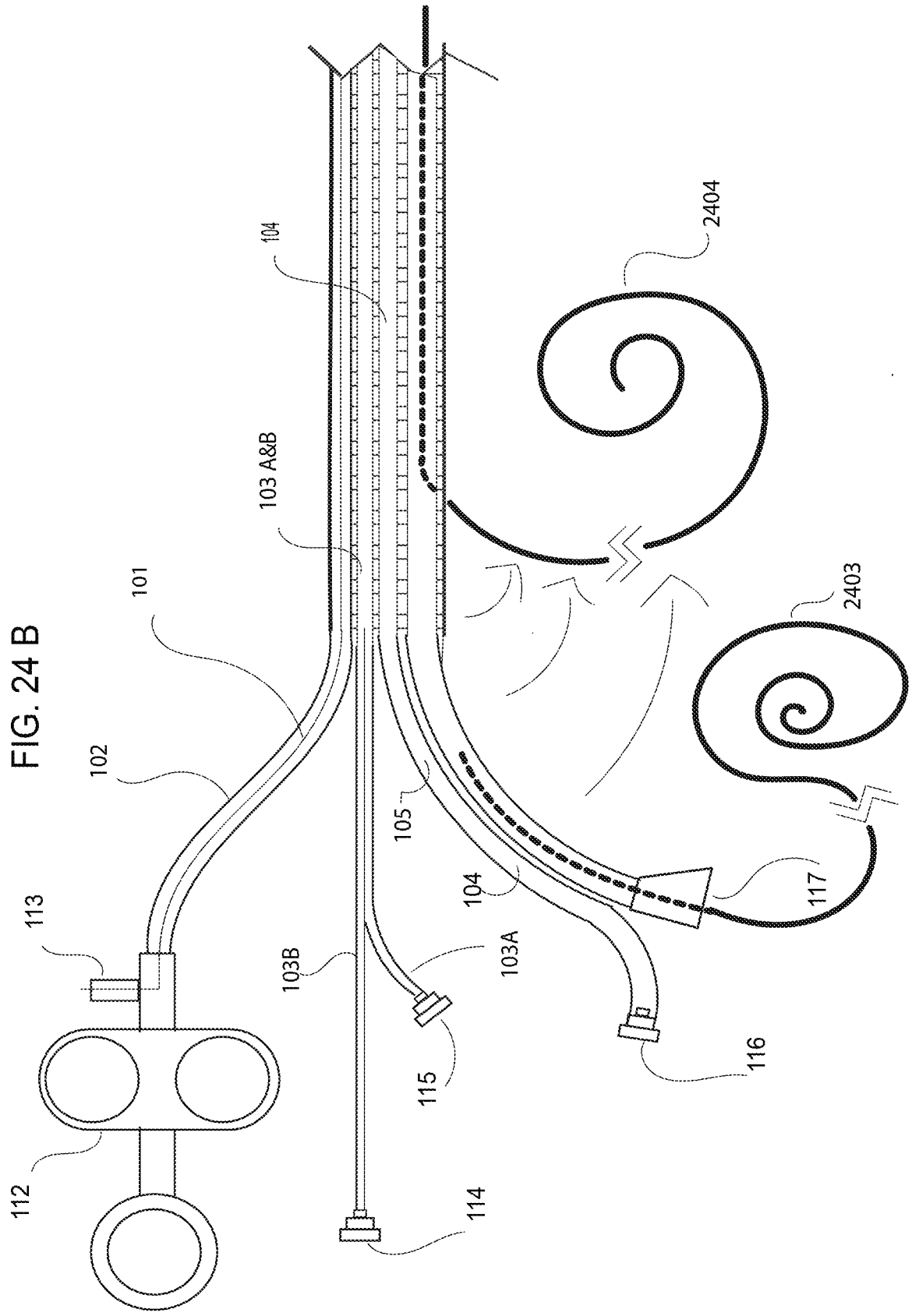

MULTI-PURPOSE MEDICAL DEVICE FOR STREAMLINED BILIARY AND OTHER INTERVENTIONS

REFERENCES CITED

US Patent Documents

| | | |
|---|---|---|
| 5,035,696 A | July 1991 | Rydell |
| 5,024,617 A | June 1991 | Karpiel et al. |
| 7,947,056 B2 | May 2011 | Griego et al. |
| 8,579,895 B2 | November 2013 | Hutchins et al. |
| 5,599,300 A | April 1997 | Weaver et al. |
| 4,906,241 A | March 1990 | Noddin et al. |
| 6,896,842 B1 | May 2005 | Hamilton et al. |
| 7,147,631 B2 | December 2006 | Scopton. |
| 7,481,800 B2 | January 2009 | Jacques. |
| 8,591,563 B2 | November 2013 | Karpiel et al., |
| 4,988,356 A | January 1991 | Crittenden et al. |
| 7,147,631 B2 | December 2006 | Scopton. |
| 8,206,320 B2 | June 2012 | Deal et al., |
| 8,512,389 B2 | August 2013 | Ayala et al |
| 5,547,469 A | August 1996 | Rowland et al. |
| 6,692,484 B1 | February 2004 | Karpiel et al. |

Other Publications

1. Sripathi R K et al. Technology status evaluation report: ERCP cannulation and sphincterotomy devices. Gastrointest Endosc. 2010; 71(3): 435-445.
2. Shah R J et al. Short-wire ERCP systems. Gastrointest Endosc. 2007; (66)4:650-657.
3. Gilmara C M, Baron T H. Endoscopic papillary large-balloon dilation combined with endoscopic biliary sphincterotomy for the removal of bile duct stones (with video). Gastrointest Endosc. 2011; 74(5):1119-1126.
4. Kim T H et al. international consensus guidelines for endoscopic papillary large-balloon dilation. *Gastrointestinal Endosc.* 2015; 83(1); 37-47.
5. Bauxbaum J L et al. ASGE guideline on the role of endoscopy in the evaluation and management of choledocholithiasis. Gastrointest Endosc. 202; 94(2):222-234.
6. Desai M et al. ASGE innovations to improve endoscopic practice: A detailed and prospective analysis of the environmental impact of waste generation and energy consumption from GI procedures. Gastrointest Endosc. 2023; 97(6S):AB696.

BACKGROUND OF THE INVENTION

The migration of a stone from the gallbladder into the bile duct can lead to serious morbidity and mortality related to biliary obstruction, obstructive jaundice, acute suppurative cholangitis, sepsis and gallstone pancreatitis. Before the advent of endoscopic retrograde cholangiopancreatography (ERCP), stone extraction required laparotomy and open common bile duct exploration, a surgery that was associated with significant mortality, morbidity and a prolonged hospital stay. With the advent of ERCP, the stone extraction can be accomplished by a gastroenterologist as an outpatient procedure with minimal risks. The first ERCP was performed, not by a gastroenterologist but by an Obstetrician, Dr. William McCune in 1968. The procedure was subsequently advanced popularized by Dr. Peter Cotton, Dr. Meinhard Classen and Dr. Keiichi Kawai in the 70s.

The ERCP procedure involves the introduction of a side-viewing endoscope called the duodenoscope through the mouth and advancement into the second portion of the duodenum, with the patient positioned semi-prone on an x-ray table for fluoroscopic imaging. The tip of the duodenoscope is aligned with the bile duct and pancreatic duct openings at a shared protuberance called the ampulla of Vater. The ampulla of Vater has an opening called the ampullary orifice surrounded by a sphincter muscle called the sphincter of Oddi.

A typical stone extraction procedure currently involves introduction of a multiple lumen catheter called a sphincterotome through the working channel of a duodenoscope that has a lumen for injecting contrast, a lumen for advancing a guidewire through it/advancing it over a guidewire and a cutting wire assembly.[1,2] The wire assembly consists of conductive (cutting) and non-conductive portions, attached distally to the distal end of the catheter via anchors and extending proximally through one of the lumens near the surface to be attached to a handle at the proximal end of the catheter. A short portion of the wire immediately proximal to the tip is external to the catheter and contains the cutting part. Operation of the handle allows the wire to be manipulated resulting in tip deflection into or out of a curved configuration facilitating contact between the exposed electrosurgical wire and the sphincter of Oddi. The bile duct is cannulated with the tip of the catheter and contrast is injected through the catheter for fluoroscopic imaging of the bile duct. A sphincterotomy is done to cut the opening of the bile duct. For most significant sized stones, balloon dilation of the ampulla is required to facilitate stone extraction. To accomplish this, the first catheter is removed, and a second catheter is advanced over the guidewire that has a dilator balloon near the distal end. Infusion of fluid distends the dilator balloon to stretch and expand the ampullary orifice and the biliary outflow tract. This catheter is removed, and a third catheter is then advanced over the guidewire into the bile duct that has a stone extraction balloon at the distal end. The tip of the catheter is advanced past the stone in the bile duct, the balloon is inflated with air and the catheter with the inflated balloon is pulled out to sweep the stone out of the bile duct into the duodenal lumen to be excreted out.

The dilator balloon and the stone extraction balloon are quite different from each other and serve distinctly different functions. The dilator balloon is a low-compliance, high-pressure balloon that is typically composed of PET (polyethylene terephthalate), nylon, Pebax or other similar materials, and has high hoop strength to achieve high dilating forces. This balloon is filled under pressure with the infusion a fluid through a lumen that extends proximally from the balloon to the proximal end of the catheter. It is filled under pressure with a fluid e.g., diluted contrast material, normal saline or sterile water to expand the balloon to a predetermined diameter to dilate the ampulla of Vater. This process expands the biliary passage and smooths out any kinks or angulations to facilitate passage of large bile duct stones during a subsequent stone extraction maneuver. The stone extraction balloon, on the other hand, is low-pressure, high-compliance balloon. It is filled through a lumen that extends proximally from the balloon to the proximal end of the catheter. It has an attachment at the proximal end to be attached to a syringe filled with air. Such high compliance balloons are typically composed of silicone, latex, polyurethane and other similar materials. Such balloons are soft and deformable and conform to the shape of the lumen. These balloons are ideal for sweeping an object out of a body lumen but are not suitable for dilation as they lack the strength needed to achieve high dilating forces.

Balloon dilation of the ampulla after biliary sphincterotomy has become increasingly popular among skilled gastroenterologists as it makes the process of stone extraction easier and safer. This technique also referred to as endoscopic papillary large-balloon dilation (EPLBD) or dilation assisted stone extraction (DASE). DASE has been shown to be superior to sphincterotomy alone for complete endoscopic stone clearance during the first session (initial success rate) and final success rate.[3,4,5] Furthermore, the higher success rate has been demonstrated to be accomplished with a shorter procedure time and lower radiation exposure. It has also been shown to be associated with lower need for mechanical lithotripsy and lower overall complications rate. In a technical review and metanalysis, Gilmara and Baron found high initial success rates (91%) and final success rates (98%) for complete clearance of large and difficult bile duct stones by using combined endoscopic sphincterotomy and endoscopic large balloon dilation.[3] The need for mechanical lithotripsy was 9.3% and lower than that reported for endoscopic sphincterotomy alone (15%) and endoscopic papillary balloon dilation alone (21%). The rates of post ERCP pancreatitis, bleeding, and overall adverse events with combined endoscopic sphincterotomy and endoscopic papillary balloon dilation were 2.8%, 1.2%, and 5%, respectively, compared with 4.3%, 4.8%, and 12.7% with endoscopic sphincterotomy alone and 8.6%, 0.1%, and 12.1% with endoscopic papillary balloon dilation alone.

International consensus guidelines by Kim et al also concluded that endoscopic papillary balloon dilation with endoscopic sphincterotomy can reduce the need for endoscopic mechanical lithotripsy and its attendant complications.[4]

ASGE standards of practice committee conducted a metanalysis of 22 observational comparative reports in addition to 9 RCTs (endoscopic sphincterotomy followed by large balloon dilation 1939 patients; endoscopic sphincterotomy alone, 2148 patients).[5] There was greater overall clearance (OR, 2.33 [95% Cl, 1.66-3.28], and first procedure clearance (OR, 2.09 [95% Cl, 1.41-3.09] in the endoscopic sphincterotomy followed by large balloon dilation cohorts. The official ASGE guideline by Bauxbaum et al. concluded: "Recommendation: In patients with large bile duct stones, we suggest performing endoscopic sphincterotomy followed by large balloon dilation (ES-LBD) rather than endoscopic sphincterotomy alone (conditional recommendation, moderate evidence)."

With increasing experience with this technique, many gastroenterologists find DASE to be increasingly useful even when a stone does not appear to be large on initial assessment as it makes the stone extraction process smoother and faster and eliminates the need for unanticipated forceful and sometime awkward balloon sweeps. Gastroenterologists are often faced with situations when balloon sweeps are done after sphincterotomy, and no stones are retrieved but significant resistance is encountered during the balloon sweeps. It could represent a stone impacted eccentrically in the bile duct. It is difficult to confidently declare "ductal clearance" under such circumstances. Balloon dilation of the ampulla prior to the balloon sweeps generally eliminates this problem. One can then be confident that there are no retained stones that may result in recurrent symptoms, additional procedures and hospitalizations.

Dilating balloons specifically designed for the biliary system have a maximum diameter of 10 mm. For large balloon dilation of the ampulla, typically non-biliary, esophageal/pyloric dilating balloon are used, either single diameter or more popularly multi-diameter (staged inflation) balloons. These come in typical balloon lengths of 5 cm to 8.5 cm and the commonly used diameters are 12-13.5-15 and 15-16.5-18-mm diameter in multi-diameter balloons. Balloons of this length are not optimal for endoscopic papillary large balloon dilation as balloons of this length may be awkward to position in the duodenum or may extend too much into the bile duct and potentially cause bile duct injury by pressing stone fragments against the bile duct wall. Specific biliary large diameter balloons of smaller length, probably 2-4 cm long, would be optimal for dilation assisted stone extraction (DASE).

The process of stone extraction is a time-consuming process that requires multiple catheters and multiple exchanges. There has been a lot of effort devoted towards making this process faster and easier with multiple modifications of the wire exchange system with variable but limited success.[2] There is a pressing need to develop a catheter that can perform all three functions so there is no need for cumbersome catheter exchanges. This would reduce valuable procedure time for the healthcare system and healthcare providers and thereby improve efficiency. It would reduce the time a patient has to be under anesthesia, thereby reducing the risk of anesthesia related complications. The use of one catheter to replace three catheters would significantly reduce healthcare costs and even more importantly reduce medical waste generation.

It is being increasingly recognized that the gastrointestinal endoscopic procedures are a significant source of environmental waste generation. In a single center prospective study conducted on consecutive patients, the authors analyzed waste generation for 450 consecutive procedures over a two-month period.[6] The total waste generated during this time period was 1398.6 kg; 61.6% directly going to landfill, 33.3% biohazard waste and 5.1% sharps. The average per procedure waste directly going to landfill was 2.19 kg which approximates to 9,189 kg for an entire year or 219 kg/100 procedures. In total, the annual waste generation from a single center approximated the size of two football fields. The authors concluded that these data could serve as an actionable model for health-systems to reduce total waste generation, landfill and water waste towards environmentally sustainable endoscopy units.

There is a strong need to develop endoscopic devices that can perform multiple tasks so that one device or catheter can be used to accomplish a task that that normally requires two or three separate devices or catheters. The object of the current invention was to address all these concerns and develop one catheter that can serve all three functions, eliminating the need for multiple catheters and catheter exchanges.

To review prior art relevant to the current invention, sphincterotomy catheters have been around for decades as described by U.S. Pat. No. 5,035,696 to Rydell and U.S. Pat. No. 5,024,617 to Karpiel et al. Modifications have subsequently been made to the sphincterotome design to make them steerable, rotatable, lockable and safer to use as disclosed by U.S. Pat. No. 7,947,056 to Griego et al. and U.S. Pat. No. 8,579,895 B2 to Hutchins et al. Needle knife papillotomes were developed for cutting directly into the bile duct in cases of difficult cannulation as described by U.S. Pat. No. 5,599,300 to Weaver et al. Catheters with dilation balloons were developed and modified as disclosed by U.S. Pat. No. 4,906,241 to Noddin et al., U.S. Pat. No. 6,896,842 B1 to Hamilton et al. and U.S. Pat. No. 7,147,631

B2 to Scopton. Multi-lumen stone extraction balloon catheters were developed as disclosed by U.S. Pat. No. 7,481, 800 B2 to Jacques.

The different catheters are typically exchanged over a guidewire. The traditional long-wire exchange technique requires an extra-long guidewire, usually 460 or 480 cm in length and requires a carefully coordinated exchange process between the gastroenterologist and the assistant. The Short-wire (rapid exchange) systems were developed as disclosed by U.S. Pat. No. 8,591,563 B2 to Karpiel et al., U.S. Pat. No. 4,988,356 to Crittenden et al. and U.S. Pat. No. 7,147,631 B2 to Scopton. In this technique, the guidewire is coupled for only a portion of the catheter length and a shorter guidewire can be used, typically 260 cm in length. This shortens the exchange time and gives the gastroenterologist more control over the wire. Ultra-short wire systems were developed for intraductal exchange as disclosed by U.S. Pat. No. 8,206,320 B6 to Deal et al. and U.S. Pat. No. 8,512,389 to Ayala et al. In this technique, the primary access device is coupled to the guidewire for a very short distance, such as the distal 6 cm, with the guidewire exiting at that point through a side port. The wire exchange can thus be performed entirely within the bile duct by advancing the catheter or pulling back on the guidewire until uncoupling is accomplished within the bile duct. A shorter guidewire is needed, typically 185 cm in length.

Other developments have been made to design multipurpose catheters to reduce the number of catheter exchanges as disclosed by U.S. Pat. No. 5,547,469 to Rowland et al. A stone extraction balloon is mounted on a sphincterotome. This would work well for small stones. However, for large stones or stones with sharp edges when balloon dilation of the ampulla is required, two separate catheters and two separate catheter exchanges are still required. A catheter housing a dilator balloon and either an extractor balloon, or a basket is disclosed in U.S. Pat. No. 6,692,484 B1 to Karpiel et al. Another catheter for sphincterotomy and another catheter exchange is again required.

SUMMARY OF THE INVENTION

The object of the current invention is to address the above-mentioned concerns and develop a catheter that can serve multiple functions, eliminating the need for multiple catheters and multiple catheter exchanges. The current invention provides an apparatus for, and a method of, performing multiple interventions within the biliary tree, or another body lumen, without requiring multiple catheter exchanges. All the steps essential for successful stone extractions can be performed using a single catheter without requiring any catheter exchanges, saving valuable procedure time, cutting medical costs and minimizing medical waste.

The invention consists of a flexible, multi-lumen elongate tube designed to be introduced through the working channel of a duodenoscope, or another suitable endoscope/sheath/port/device, into the bile duct or another body lumen. In the exemplary case of the biliary system, it has a proximal end towards the operator and the distal end designed to exit the distal end of the duodenoscope towards the ampulla of Vater/biliary orifice. It is an elongate cylindrical catheter with a smooth tapering at the tip to facilitate entry into the bile duct. It consists of a plurality of independent lumens, running parallel to each other in general, extending the entire length, or most of the length of the catheter. One of the lumens may have a large enough diameter to allow the passage of a 0.035 inch or a 0.025 inch guidewire. With improvements in guidewire materials, design and maneuverability, 0.025 inch guidewire has become more useful may become the new standard guidewire. It is possible that even a smaller diameter guidewire lumen may have utility in the future with further improvements in guidewire design. The other lumens can be quite small, and some of the lumens can be arranged along the periphery and/or have non-circular cross-sectional shapes to optimally utilize the space within the catheter. Two of the lumens extend from the proximal end to the distal end, one configured to accept a guidewire, and the other to allow injection of contrast. In some embodiments, one lumen may be configured to serve both functions. The exposed part of an electrosurgical cutting wire near the distal end is used to cut the sphincter of Oddi. In some embodiments of the invention, the cutting wire assembly is in the form a pull-type sphincterotome. In this configuration, the wire assembly consists of conductive (cutting) and non-conductive portions, attached distally to the distal end of the catheter via anchors and extending proximally through one of the lumens near the surface to be attached to a handle at the proximal end of the catheter. A short portion of the wire immediately proximal to the tip is external to the catheter and contains the cutting part. Operation of the handle allows the wire to be manipulated resulting in tip deflection into or out of a curved configuration facilitating contact between the exposed electrosurgical cutting wire and the sphincter of Oddi. In other embodiments of the invention, the electrosurgical wire is in a needle-knife configuration. In this configuration the cutting part of the wire is at the tip, and manipulation of the handle allows the tip of the electrosurgical wire to slide in and out to the distal tip of the catheter. This allows the catheter to cut directly into the bile duct when cannulation of the bile duct is not feasible because of difficult anatomy.

The various embodiments should be compatible with handle systems/cutting wire assemblies that are currently available or may become available in the future including but not limited to those with steerable/non-steerable, rotating/non-rotating, locking/non-locking tip-deflection and tip-manipulation mechanisms. The wire may be constructed from any of the currently available materials like stainless steel, nitinol, tungsten or any materials that may become available in the future. Each of the illustrative embodiments of the catheter houses a low-compliance, high-pressure dilator balloon on the distal shaft. Such balloons are typically composed of PET (polyethylene terephthalate), nylon, Pebax or other similar materials, and have high hoop strength to achieve high dilating forces. This balloon is filled under pressure with the infusion of a fluid through a lumen that extends proximally from the balloon to the proximal end of the catheter. It has a luer lock or another compatible connector at the proximal end to be attached to an inflation device/fluid filled syringe with a pressure gauge. It is filled under pressure with a fluid e.g., diluted contrast material, normal saline or sterile water to expand the balloon to a predetermined diameter to dilate the ampulla of Vater. It may be configured to be inflated to a single diameter or several different diameters (multi-diameter) based on the pressure level achieved with the amount of the fluid administered (staged inflation). This process would expand the biliary passage and smooth out any kinks or angulations to facilitate passage of large bile duct stones during a subsequent stone extraction maneuver. Each of the embodiments of the catheter also houses a second low-pressure, high compliance balloon located more distally on the shaft for stone extraction/retrieval. It is filled independently through a separate lumen that extends proximally from the balloon to the proximal end of the catheter. It has a connector at the proximal end to be attached to a syringe filled with air. It can be configured to be inflated to one fixed or several predetermined diameters based on the volume of air introduced. Such low-pressure, high compliance balloons are typically composed of silicone, latex, urethane and other similar materials. Such balloons are soft and deformable, ideal for sweeping an object out of a body lumen but are not suitable for dilation as they lack the strength to achieve high dilating forces. When a retrieval balloon is positioned proximal to a bile duct stone, inflated and pulled out of the bile duct, it would sweep the stone easily and smoothly out of the bile duct through a passage that has already been cut with a cutting wire and further dilated with a dilator balloon. The catheter of this device may be constructed from any of a wide variety of suitable materials or blend of materials that are currently available such as nylon, teflon, silicone, polyurethane, polyethylene or polyvinyl chloride (PVC), or other materials that may become available in the future. It may be constructed in a variety of possible designs, capable of being used with a long-wire system, a short-wire system or the ultra-short wire/intraductal exchange system.

In one illustrative embodiment, the invention consists of a flexible elongate tube with a proximal end towards the operator and a distal end towards the ampullary orifice with a cutting wire assembly in the form of a pull-type sphincterotome. The wire assembly consists of conductive cutting and non-conductive portions, attached distally to the distal end of the catheter via anchors and extending proximally through one of the lumens near the surface to be attached to a handle at the proximal end of the catheter. A short portion of the wire immediately proximal to the tip is external to the catheter and contains the cutting part. Operation of the handle allows the wire to be manipulated resulting in tip deflection into or out of a curved configuration facilitating contact between the exposed electrosurgical wire and the sphincter of Oddi. A second lumen extends from the proximal end of the catheter to the distal tip, configured for injection of contrast material into the biliary tree, needed for fluoroscopic imaging of the biliary tree. A third lumen extends from the proximal end of the catheter towards the distal tip, configured to accept a guidewire, needed for introduction of the guidewire into the biliary or pancreatic duct. It may be in a long-wire configuration or have a channel configured for short-wire exchange. It may have an additional side opening (side-port) near the distal tip to be used for ultra-short wire/intraductal exchange. It houses a low-compliance, high-pressure dilator balloon on the distal shaft. This balloon is filled under pressure with the infusion a fluid through a lumen that extends proximally from the balloon to the proximal end of the catheter. It has a luer lock or another compatible connector at the proximal end to be attached to an inflation device/fluid filled syringe with a pressure gauge. It is filled under pressure with a fluid e.g., diluted contrast material, to expand the balloon to a predetermined diameter to dilate the ampulla of Vater. It may be configured to be inflated to a single diameter or several different diameters (multi-diameter) based on the pressure level achieved with the amount of the fluid administered (staged inflation). The catheter also houses a second low pressure, high compliance balloon located more distally on the shaft for stone extraction/retrieval. It is filled independently through a separate lumen that extends proximally from the balloon to the proximal end of the catheter. It has a connector at the proximal end to be attached to a syringe filled with air. It can be configured to inflated to one fixed or several predetermined diameters based on the volume of air introduced. When a retrieval balloon is positioned proximal to a bile duct stone, inflated and pulled out of the bile duct, it would sweep the stone easily and smoothly out of the bile duct through a passage that has already been cut with a cutting wire and further dilated with a dilator balloon.

In another illustrative embodiment the invention consists of a flexible elongate tube with a proximal end towards the operator and a distal end towards the ampullary orifice with a cutting wire assembly in the form of a needle-knife papillotome. The wire assembly consists of conductive cutting and non-conductive portions, the cutting part is at the distal tip of the wire. In this configuration the manipulation of the handle allows the tip of the electrosurgical wire to slide in and out to the distal tip of the catheter. This allows the catheter to cut into the bile duct directly when cannulation of the bile duct is not feasible because of difficult anatomy. A second lumen extends from the proximal end of the catheter to the distal tip, configured for injection of contrast material into the biliary tree, needed for fluoroscopic imaging of the biliary tree. A third lumen extends from the proximal end of the catheter towards the distal tip, configured to accept a guidewire, needed for introduction of the guidewire into the biliary or pancreatic ducts. It may be in a long-wire configuration or have a channel configured for short-wire exchange. It may have an additional side opening (side-port) near the distal tip to be used for ultra-short wire/intraductal exchange. It houses a low-compliance, high-pressure dilator balloon on the distal shaft. This balloon is filled under pressure with the infusion a fluid through a lumen that extends proximally from the balloon to the proximal end of the catheter. It has a luer lock or another compatible connector at the proximal end to be attached to an inflation device/fluid filled syringe with a pressure gauge. It is filled under pressure with a fluid e.g., diluted contrast material, to expand the balloon to a predetermined diameter to dilate the ampulla of Vater. It may be configured to be inflated to a single diameter or several different diameters (multi-diameter) based on the pressure level achieved with the amount of the fluid administered (staged inflation). The catheter also houses a second lower pressure, high compliance balloon located more distally on the shaft for stone extraction/retrieval. It is filled independently through a separate lumen that extends proximally from the balloon to the proximal end of the catheter. It has a connector at the proximal end to be attached to a syringe filled with air. It may be configured to be inflated to one fixed or several predetermined diameters based on the volume of air introduced. When a retrieval balloon is positioned proximal to a bile duct stone, inflated and pulled out of the bile duct, it would sweep the stone easily and smoothly out of the bile duct. This catheter would obviate the need for multiple exchanges to a pull-type sphincterotome, a separate dilator balloon and a separate extractor balloon once bile duct access has been achieved.

In another illustrative embodiment the invention consists of a flexible elongate tube with a proximal end towards the operator and a distal end towards the ampullary orifice with a cutting wire assembly in the form of a pull-type sphincterotome. The wire assembly consists of conductive cutting and non-conductive portions, attached distally to the distal end of the catheter via anchors and extending proximally through one of the lumens near the surface to be attached to a handle at the proximal end of the catheter. A short portion of the wire immediately proximal to the tip is external to the catheter and contains the cutting part. Operation of the handle allows the wire to be manipulated resulting in tip deflection into or out of a curved configuration facilitating contact between the exposed electrosurgical wire and the sphincter of Oddi. A second lumen extends from the proximal end of the catheter to the distal tip, configured for injection of contrast material into the biliary tree and to accept a guidewire. The embodiment eliminates one of the lumens to save space. A Tuohy-Borst adapter may be built in or attached to the proximal end of the lumen to prevent contrast leakage/back-flow during contrast injection. It houses a low-compliance, high-pressure dilator balloon on the distal shaft. This balloon is filled under pressure with the infusion a fluid through a lumen that extends proximally from the balloon to the proximal end of the catheter. It has a luer lock or another compatible connector at the proximal end to be attached to an inflation device/fluid filled syringe with a pressure gauge. It is filled under pressure with a fluid e.g., diluted contrast material, to expand the balloon to a predetermined diameter to dilate the ampulla of Vater. It may be configured to be inflated to a single diameter or several different diameters (multi-diameter) based on the pressure level achieved with the amount of the fluid administered (staged inflation). The catheter also houses a second lower pressure, high compliance balloon located more distally on the shaft for stone extraction/retrieval. It is filled independently through a separate lumen that extends proximally from the balloon to the proximal end of the catheter. It has a connector at the proximal end to be attached to a syringe filled with air. It can be configured to be inflated to one fixed or several predetermined diameters based on the volume of air introduced.

In another illustrative embodiment the invention consists of a flexible elongate tube with a proximal end towards the operator and a distal end towards the ampullary orifice with a cutting wire assembly in the form of a needle-knife papillotome. The wire assembly consists of conductive cutting and non-conductive portions, the cutting part is at the distal tip of the wire. In this configuration the manipulation of the handle allows the tip of the electrosurgical wire to slide in and out to the distal tip of the catheter. This allows the catheter to cut into the bile duct directly when cannulation of the bile duct is not feasible because of difficult anatomy. A second lumen extends from the proximal end of the catheter to the distal tip, configured for injection of contrast material into the biliary tree and to accept a guidewire. The embodiment eliminates one of the lumens to save space. A Tuohy-Borst adapter may be built in or attached to the proximal end of the lumen to prevent contrast leakage/back-flow during contrast injection. It houses a low-compliance, high-pressure dilator balloon on the distal shaft. This balloon is filled under pressure with the infusion a fluid through a lumen that extends proximally from the balloon to the proximal end of the catheter. It has a luer lock or another compatible connector at the proximal end to be attached to an inflation device/fluid filled syringe with a pressure gauge. It is filled under pressure with a fluid e.g., diluted contrast material, to expand the balloon to a predetermined diameter to dilate the ampulla of Vater. It may be configured to be inflated to a single diameter or several different diameters (multi-diameter) based on the pressure level achieved with the amount of the fluid administered (staged inflation). The catheter also houses a second lower pressure, high compliance balloon located more distally on the shaft for stone extraction/retrieval. It is filled independently through a separate lumen that extends proximally from the balloon to the proximal end of the catheter. It has a connector at the proximal end to be attached to a syringe filled with air. It can be configured to be inflated to one fixed or several predetermined diameters based on the volume of air introduced.

BRIEF DESCRIPTION OF THE DRAWINGS

The embodiments of the present disclosure are depicted in the figures, the features and advantages will be more apparent from a reading of the detailed description in the following section. The figures are schematic and not intended to be drawn to scale. The locations, shapes and sizes of each lumen can be modified. The transverse cross-sectional views are true cross-sectional views along the transverse axis of the catheter at the respective lines. The side sectional views are not true longitudinal section views along a particular plane but are modified drawings to facilitate visual comprehension of the catheter. These drawings can be imagined as longitudinal sections cut along the axis of the wire assembly, with the lumens 103 A and 103 B added-in to have all essential parts represented in one view. Otherwise, these two lumens being located more peripherally would not be visible in a true longitudinal sectional view at the level of the wire assembly.

FIG. 1A depicts a side sectional view of the distal part of the first embodiment of the catheter.

FIG. 1 B depicts a side sectional view of the proximal part of the same embodiment of the catheter shown in FIG. 1A.

FIG. 2 depicts a cross-sectional view of a portion of the catheter of FIG. 1A taken along line 2-2.

FIG. 3 depicts a cross-sectional view of a portion of the catheter of FIG. 1A taken along line 3-3.

FIG. 4 depicts a cross-sectional view of a portion of the catheter of FIG. 1A taken along line 4-4.

FIG. 5 depicts a cross-sectional view of a portion of the catheter of FIG. 1 B taken along line 5-5.

FIG. 8 is a merged view of FIG. 1A and FIG. 1 B depicting the proximal and distal end of the first embodiment of the catheter aligned in one view.

FIG. 9A depicts a side sectional view of the distal part of the second embodiment of the catheter.

FIG. 9 B depicts a side sectional view of the proximal part of the same embodiment of the catheter shown in FIG. 9A.

FIG. 10 depicts a cross-sectional view of a portion of the catheter of FIG. 9A taken along line 10-10.

FIG. 11 depicts a cross-sectional view of a portion of the catheter of FIG. 9A taken along line 11-11.

FIG. 12 depicts a cross-sectional view of a portion of the catheter of FIG. 9A taken along line 12-12.

FIG. 13 depicts a cross-sectional view of a portion of the catheter of FIG. 9 B taken along line 13-13.

FIG. 14A depicts a side sectional view of the distal part of the third embodiment of the catheter.

FIG. 14 B depicts a side sectional view of the proximal part of the same embodiment of the catheter shown in FIG. 14A.

FIG. 15 depicts a cross-sectional view of a portion of the catheter of FIG. 14A taken along line 15-15.

FIG. 16 depicts a cross-sectional view of a portion of the catheter of FIG. 14A taken along line 16-16.

FIG. 17 depicts a cross-sectional view of a portion of the catheter of FIG. 14A taken along line 17-17.

FIG. 18 depicts a cross-sectional view of a portion of the catheter of FIG. 14 B taken along line 18-18.

FIG. 19A depicts a side sectional view of the distal part of the fourth embodiment of the catheter.

FIG. 19 B depicts a side sectional view of the proximal part of the same embodiment of the catheter shown in FIG. 19A.

FIG. 20 depicts a cross-sectional view of a portion of the catheter of FIG. 19A taken along line 20-20.

FIG. 21 depicts a cross-sectional view of a portion of the catheter of FIG. 19A taken along line 21-21.

FIG. 22 depicts a cross-sectional view of a portion of the catheter of FIG. 19A taken along line 22-22.

FIG. 23 depicts a cross-sectional view of a portion of the catheter of FIG. 19 B taken along line 23-23.

FIG. 24A depicts a side sectional view of the distal part of the first embodiment of the catheter demonstrating different ways a guidewire can be loaded.

DETAILED DESCRIPTION OF THE INVENTION

Figure 7:
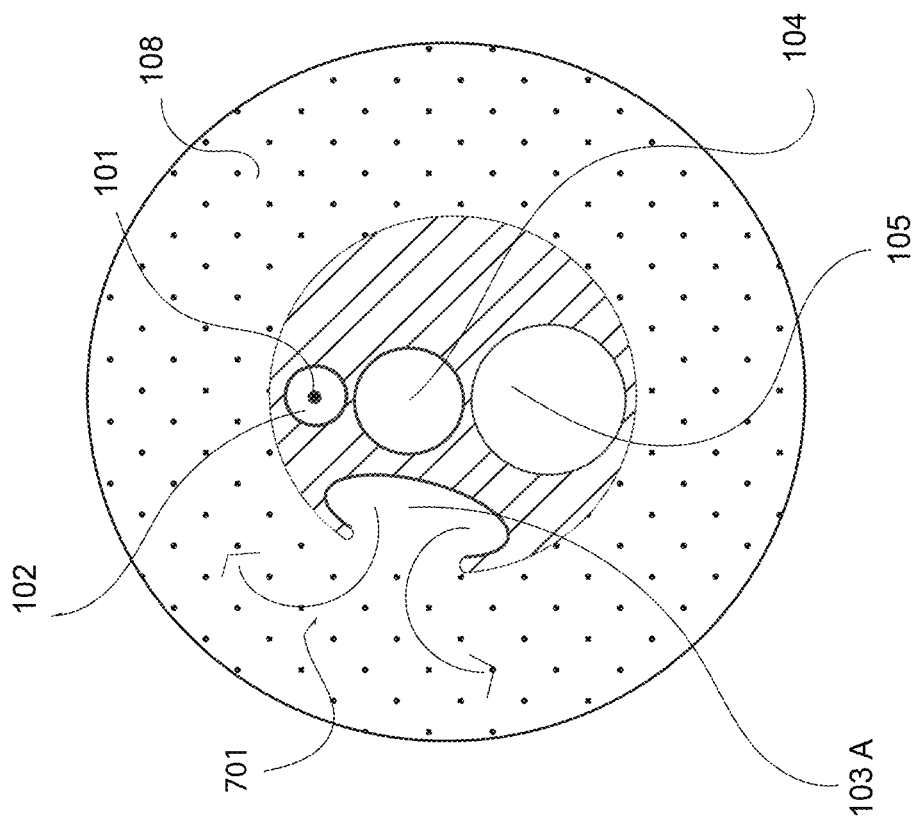
FIG. 7 depicts a cross-sectional view of a portion of the catheter of FIG. 1A taken along line 7-7 at the level of the stone extractor balloon.

The various embodiments of the present disclosure are depicted in the figures. The figures are schematic and not intended to be drawn to scale. The cross-sectional views are true cross-sectional views along the transverse axis of the catheter at the respective lines. The side sectional views are not true longitudinal section views along a particular plane but are modified drawings to facilitate visual comprehension of the catheter. These drawings can be imagined as longitudinal sections cut along the axis of the wire assembly, with the lumens 103 A and 103 B added-in to have all essential parts represented in one view. Otherwise, these two lumens being located more peripherally would not be visible in a true longitudinal sectional view at the level of the wire assembly.

FIG. 1A depicts a side sectional view of the distal part of the first embodiment of the catheter. A wire assembly 101 is depicted that is attached to the catheter near the distal tip and has cutting (conductive) part exposed to the outside near the distal tip and a non-conductive part that extends proximally through lumen 102 towards the proximal end to be attached to a handle that controls tip deflection. Lumen 104 extends from the distal tip to the proximal end, configured to accept contrast injection through the proximal end. Contrast exits the lumen at the distal tip to fill the bile duct or the pancreatic duct for fluoroscopic imaging. Lumen 105 is the lumen with the largest diameter configured to accept a guidewire, it extends from the distal tip to the proximal end. The catheter may be configured to be preloaded with a guidewire if desired. It may be configured to be part of a long-wire or a short-wire system. Additionally, it may have a side hole (side-port) near the distal tip depicted by dashed lines 111 for guidewire acceptance to be compatible with an ultra-short wire system for intraductal exchange. Lumens 103 A & B are two separate lumens for independent inflation and deflation of two separate balloons. These are not visible as separate lumens on side sectional view because of the limitations of a two-dimensional figure. These can be clearly appreciated as separate, parallel lumens on subsequent cross-sectional views. The catheter houses a low-compliance, high-pressure dilator balloon 109 on the distal shaft. This balloon is filled under pressure with the infusion a fluid through lumen 103 B that extends proximally from the balloon to the proximal end of the catheter. It has side holes 107 to allow the entry and exit of fluid from the lumen into the dilator balloon. It is filled under pressure with a fluid e.g., diluted contrast material, to expand the balloon to a predetermined diameter to dilate the ampulla of Vater. It may be configured to be inflated to a single diameter or several different diameters (multi-diameter) based on the pressure level achieved with the amount of the fluid administered (staged inflation). The catheter also houses a second low-pressure, high-compliance balloon 108 located more distally on the shaft for stone extraction/retrieval. It is filled independently through a separate lumen 103 A that extends proximally from the balloon to the proximal end of the catheter. It has side holes 106 to allow the entry and exit of air from the lumen into the extractor balloon. It can be configured to be inflated to one fixed or several different predetermined diameters based on the volume of air introduced. Radiopaque markers 110 may be placed to mark the proximal and distal end of the dilator balloon for optimal positioning of the catheter under fluoroscopy. The catheter, however, can also be positioned at the ampullary orifice under visual endoscopic guidance. Additional fluoroscopic markers may be placed as desired, for example at the proximal end of the stone extractor balloon and at the site of the distal side hole (side-port) to facilitate intraductal exchange. Color coded visual markers may be placed on the catheter at various locations as desired for guidance under endoscopic view.

FIG. 1 B depicts a side sectional view of the proximal part of the same embodiment of the catheter shown in FIG. 1A. Wire assembly 101 extends through lumen 102 to be attached to the handle 112 that controls the movements of the wire and distal tip deflection. The wire connects to a RF heating source through a RF connector 113. Lumen 103 B from the dilator balloon extends to the proximal end of the catheter and it has a luer lock or another compatible connector 114 at the proximal end to be attached to a pressure gauge and a 60-cc inflation device/fluid filled syringe (not shown). It is used to fill the dilator balloon under pressure with a fluid e.g., diluted contrast material, normal saline or sterile water, configured to inflate the balloon to one fixed diameter or several different predetermined diameters based on the pressure level achieved with the amount of the fluid administered. Lumen 103 A extends proximally from the stone extraction balloon to the proximal end of the catheter. It has a connector 115 at the proximal end to be attached to a syringe filled with air (not shown). The stone extraction balloon can be configured to be inflated to one fixed or several different predetermined diameters based on the volume of air introduced. Lumen 104 extends from the distal tip to the proximal end, configured to accept contrast injection through a connector 116 at the proximal end. Lumen 105 is the lumen with the largest diameter configured to accept a guidewire through port 117. The catheter may be configured to be preloaded with a guidewire if desired. It may be configured to a be part of long-wire system or it may have splitable channel in the form of C, U, O or other potential channels for use as a short-wire system.

FIG. 2 depicts a cross-sectional view of a portion of the catheter of FIG. 1A taken along line 2-2. A wire assembly 101 is depicted that is attached to the catheter near the distal tip and extends proximally through lumen 102 towards the proximal end of the catheter. Lumen 104 extends from the distal tip to the proximal end, configured to accept contrast injection through the proximal end. Lumen 105 is the lumen with the largest diameter configured to accept a guidewire and extends from the distal tip to the proximal end. Lumens 103 A and 103 B are two separate lumens for independent inflation and deflation of two separate balloons. These were not visible as separate lumens on side sectional view because of the limitations of a two-dimensional figure. These can be clearly appreciated as separate, parallel lumens on this cross-sectional view. The low-compliance, high-pressure dilator balloon on the distal shaft is filled under pressure with the infusion of fluid through lumen 103 B that extends proximally from the dilator balloon to the proximal end of the catheter. The low pressure, high compliance stone extraction/retrieval balloon located more distally on the shaft is filled independently through a separate lumen 103 A that extends proximally from the balloon to the proximal end of the catheter.

FIG. 3 depicts a cross-sectional view of a portion of the catheter of FIG. 1A taken along line 3-3. This cross-sectional view is distal to the dilator balloon and therefore lumen 103 B in not present. Otherwise, it is identical to FIG. 2.

FIG. 4 depicts a cross-sectional view of a portion of the catheter of FIG. 1A taken along line 4-4. This cross-sectional view is distal to the stone extraction/retrieval balloon and therefore lumen 103 A in not present. Otherwise, it is identical to FIG. 3.

FIG. 5 depicts a cross-sectional view of a portion of the catheter of FIG. 1 B taken along line 5-5. It is identical to FIG. 2.

Figure 6:
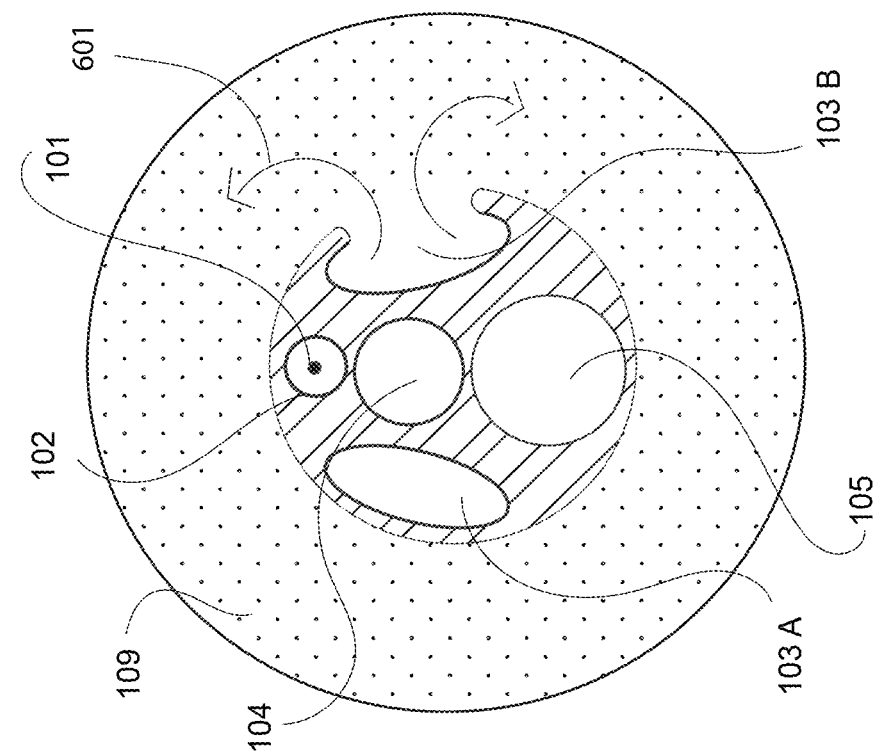
FIG. 6 depicts a cross-sectional view of a portion of the catheter of FIG. 1A taken along line 6-6 at the level of the dilator balloon.

FIG. 6 depicts a cross-sectional view of a portion of the catheter of FIG. 1A taken along line 6-6 through the middle of the low-compliance, high-pressure dilator balloon 109. Lumens 103 A and 103 B are two separate lumens for independent inflation and deflation of two separate balloons. These are not visible as separate lumens on side sectional views because of the limitations of a two-dimensional figure. These can be clearly appreciated as separate, parallel lumens on this cross-sectional view. The low-compliance, high-pressure dilator balloon on the distal shaft is filled under pressure with the infusion of fluid through lumen 103 B that extends proximally from the dilator balloon 109 to the proximal end of the catheter. The arrows 601 depict the flow of fluid, typically diluted radiographic contrast material, from lumen 103 B into the lumen of the dilator balloon 109, to distend the balloon. Fluid exits the balloon 109 into lumen 103 B during balloon deflation. The low-pressure, high-compliance stone extraction/retrieval balloon located more distally on the shaft is filled independently through a separate lumen 103 A that extends proximally from the balloon to the proximal end of the catheter. A wire assembly 101 is depicted that is attached to the catheter near the distal tip and extends proximally through lumen 102 towards the proximal end of the catheter. Lumen 104 extends from the distal tip to the proximal end, configured to accept contrast injection through the proximal end. Lumen 105 is the lumen with the largest diameter configured to accept a guidewire and extends from the distal tip to the proximal end.

FIG. 7 depicts a cross-sectional view of a portion of the catheter of FIG. 1A taken along line 7-7 through the middle of the low-pressure, high-compliance, stone extraction/retrieval balloon 108 located more distally on the catheter than the dilator balloon shown in FIG. 6. Lumen 103 B is not present anymore as it ends at the level of the low-compliance, high-pressure dilator balloon, located more proximally. The arrows 701 depict the flow of air from lumen 103 A into low-pressure, high-compliance stone extraction/retrieval balloon 108 to inflate the balloon. Air exits the balloon 108 into lumen 103 A during balloon deflation. Balloon inflation and deflation is controlled by an air-filled syringe attached to the proximal end of lumen 103A. A wire assembly 101 is depicted that is attached to the catheter near the distal tip and extends proximally through lumen 102 towards the proximal end of the catheter. Lumen 104 extends from the distal tip to the proximal end, configured to accept contrast injection through the proximal end. Lumen 105 is the lumen with the largest diameter configured to accept a guidewire and extends from the distal tip to the proximal end.

FIG. 8 is a merged view of FIG. 1A and FIG. 1 B depicting the proximal and distal end of the catheter aligned in one view.

FIG. 9A depicts a side sectional view of the distal part of the second embodiment of the catheter. The wire assembly 901 is in a needle-knife configuration. In this configuration the manipulation of the handle allows the tip of the electrosurgical wire to slide in and out to the distal tip of the catheter. This allows the catheter to cut into the bile duct directly when cannulation of the bile duct is not feasible because of difficult anatomy. The wire 901 has a cutting (conductive) part at the distal tip that slides in and out of the tip of the catheter and a non-conductive part that extends proximally through lumen 902 towards the proximal end to be attached to a handle that controls the movement of the wire. Lumen 104 extends from the distal tip to the proximal end, configured to accept contrast injection through the proximal end. Contrast exits the lumen at the distal tip to fill the bile duct or the pancreatic duct for fluoroscopic imaging. Lumen 105 is the lumen with the largest diameter configured to accept a guidewire, it extends from the distal tip to the proximal end. The catheter may be configured to be preloaded with a guidewire if desired. It may be configured to be part of a long-wire or a short-wire system. Additionally, it may have a side hole (side-port) near the distal tip depicted by dashed lines 111 for guidewire acceptance to be compatible with an ultra-short wire system for intraductal exchange. Lumens 103 A & B are two separate lumens for independent inflation and deflation of two separate balloons. These are not visible as separate lumens on side sectional view because of the limitations of a two-dimensional figure. These can be clearly appreciated as separate, parallel lumens on subsequent cross-sectional views. The catheter houses a low-compliance, high-pressure dilator balloon 109 on the distal shaft. This balloon is filled under pressure with the infusion a fluid through lumen 103 B that extends proximally from the balloon to the proximal end of the catheter. It has side holes 107 to allow the entry and exit of fluid from the lumen into the dilator balloon. It is filled under pressure with a fluid e.g., diluted contrast material, to expand the balloon to a predetermined diameter to dilate the ampulla of Vater. It may be configured to be inflated to a single diameter or several different diameters (multi-diameter) based on the pressure level achieved with the amount of the fluid administered (staged inflation). The catheter also houses a second low-pressure, high-compliance balloon 108 located more distally on the shaft for stone extraction/retrieval. It is filled independently through a separate lumen 103 A that extends proximally from the balloon to the proximal end of the catheter. It has side holes 106 to allow the entry and exit of air from the lumen into the extractor balloon. It can be configured to be inflated to one fixed or several different predetermined diameters based on the volume of air introduced. Radiopaque markers 110 may be placed to mark the proximal and distal end of the dilator balloon for optimal positioning of the catheter under fluoroscopy. The catheter, however, can also be positioned at the ampullary orifice under visual endoscopic guidance. Additional fluoroscopic markers may be placed as desired, for example at the proximal end of the stone extractor balloon and at the site of the distal side hole (side-port) to facilitate intraductal exchange. Color coded visual markers may be placed on the catheter at various locations as desired for guidance under endoscopic view.

FIG. 9 B depicts a side sectional view of the proximal part of the same embodiment of the catheter shown in FIG. 9A. Wire assembly 901 extends through lumen 902 to be attached to the handle 903 that controls the movements of the wire and the wire tip. The wire connects to a RF heating source through a RF connector 904. Lumen 103 B from the dilator balloon extends to the proximal end of the catheter and it has a luer lock or another compatible connector 114 at the proximal end to be attached to a pressure gauge and a 60-cc inflation device/fluid filled syringe (not shown). It is used to fill the dilator balloon under pressure with a fluid e.g., diluted contrast material, normal saline or sterile water, configured to inflate the balloon to one fixed diameter or several different predetermined diameters based on the pressure level achieved with the amount of the fluid administered. Lumen 103 A extends proximally from the stone extraction balloon to the proximal end of the catheter. It has a connector 115 at the proximal end to be attached to a syringe filled with air (not shown). The stone extraction balloon can be configured to be inflated to one fixed or several different predetermined diameters based on the volume of air introduced. Lumen 104 extends from the distal tip to the proximal end, configured to accept contrast injection through a connector 116 at the proximal end. Lumen 105 is the lumen with the largest diameter configured to accept a guidewire through port 117. The catheter may be configured to be preloaded with a guidewire if desired. It may be configured to a be part of long-wire system or it may have splitable channel in the form of C, U, O or other potential channels for use as a short-wire system.

FIG. 10 depicts a cross-sectional view of a portion of the catheter of FIG. 9A taken along line 10-10. A wire assembly 901 is depicted that has a cutting wire at the distal tip and a non-conductive part that extends proximally through lumen 902 towards the proximal end of the catheter. Lumen 104 extends from the distal tip to the proximal end, configured to accept contrast injection through the proximal end. Lumen 105 is the lumen with the largest diameter configured to accept a guidewire and extends from the distal tip to the proximal end. Lumens 103 A and 103 B are two separate lumens for independent inflation and deflation of two separate balloons. These were not visible as separate lumens on side sectional view because of the limitations of a two-dimensional figure. These can be clearly appreciated as separate, parallel lumens on this cross-sectional view. The low-compliance, high-pressure dilator balloon on the distal shaft is filled under pressure with the infusion of fluid through lumen 103 B that extends proximally from the dilator balloon to the proximal end of the catheter. The low pressure, high compliance stone extraction/retrieval balloon located more distally on the shaft for It is filled independently through a separate lumen 103 A that extends proximally from the balloon to the proximal end of the catheter.

FIG. 11 depicts a cross-sectional view of a portion of the catheter of FIG. 9A taken along line 11-11. This cross-sectional view is distal to the dilator balloon and therefore lumen 103 B in not present. Otherwise, it is identical to FIG. 10.

FIG. 12 depicts a cross-sectional view of a portion of the catheter of FIG. 9A taken along line 12-12. This cross-sectional view is distal to the stone extraction/retrieval balloon and therefore lumen 103 A in not present. Otherwise, it is identical to FIG. 11.

FIG. 13 depicts a cross-sectional view of a portion of the catheter of FIG. 9 B taken along line 13-13. It is identical to FIG. 10.

FIG. 14A depicts a side sectional view of the distal part of the third embodiment of the catheter. A wire assembly 101 is depicted that is attached to the catheter near the distal tip and has cutting (conductive) part exposed to the outside near the distal tip and a non-conductive part that extends proximally through lumen 102 towards the proximal end to be attached to a handle that controls tip deflection. Lumen 105 extends from the proximal end of the catheter to the distal tip, configured for injection of contrast material into the biliary tree and to accept a guidewire. The embodiment eliminates one of the lumens to save space. A Tuohy-Borst adapter may be built in or attached to the proximal end of the lumen to prevent contrast leakage. The catheter may be configured to be preloaded with a guidewire if desired. Lumens 103 A & B are two separate lumens for independent inflation and deflation of two separate balloons. These are not visible as separate lumens on side sectional view because of the limitations of a two-dimensional figure. These can be clearly appreciated as separate, parallel lumens on subsequent cross-sectional views. The catheter houses a low-compliance, high-pressure dilator balloon 109 on the distal shaft. This balloon is filled under pressure with the infusion a fluid through lumen 103 B that extends proximally from the balloon to the proximal end of the catheter. It has side holes 107 to allow the entry and exit of fluid from the lumen into the dilator balloon. It is filled under pressure with a fluid e.g., diluted contrast material, to expand the balloon to a predetermined diameter to dilate the ampulla of Vater. It may be configured to be inflated to a single diameter or several different diameters (multi-diameter) based on the pressure level achieved with the amount of the fluid administered (staged inflation). The catheter also houses a second low-pressure, high-compliance balloon 108 located more distally on the shaft for stone extraction/retrieval. It is filled independently through a separate lumen 103 A that extends proximally from the balloon to the proximal end of the catheter. It has side holes 106 to allow the entry and exit of air from the lumen into the extractor balloon. It can be configured to be inflated to one fixed or several different predetermined diameters based on the volume of air introduced. Radiopaque markers 110 may be placed to mark the proximal and distal ends of the dilator balloon for optimal positioning of the catheter under fluoroscopy. The catheter, however, can also be positioned at the ampullary orifice under visual endoscopic guidance. Additional fluoroscopic markers may be placed as desired, for example at the proximal end of the stone extractor balloon as desired. Color coded visual markers may be placed on the catheter at various locations as desired for guidance under endoscopic view.

FIG. 14 B depicts a side sectional view of the proximal part of the same embodiment of the catheter shown in FIG. 14A. Wire assembly 101 extends through lumen 102 to be attached to the handle 112 that controls the movements of the wire and distal tip deflection. The wire connects to a RF heating source through a RF connector 113. Lumen 103 B from the dilator balloon extends to the proximal end of the catheter and it has a luer lock or another compatible connector 114 at the proximal end to be attached to a pressure gauge and a 60-cc inflation device/fluid filled syringe (not shown). It is used to fill the dilator balloon under pressure with a fluid e.g., diluted contrast material, normal saline or sterile water, configured to inflate the balloon to one fixed diameter or several different predetermined diameters based on the pressure level achieved with the amount of the fluid administered. Lumen 103 A extends proximally from the stone extraction balloon to the proximal end of the catheter. It has a connector 115 at the proximal end to be attached to a syringe filled with air (not shown). The stone extraction balloon can be configured to be inflated to one fixed or several different predetermined diameters based on the volume of air introduced. Lumen 105 is the lumen with the largest diameter configured to accept a guidewire and contrast injection. A Tuohy-Borst adapter 116 may be built-in or attached to the proximal end of the lumen to prevent backflow of contrast. The silicone valve and cap 117 of the Tuohy-Borst adapter torque around the guidewire while contrast is injected through the injection port 118.

FIG. 15 depicts a cross-sectional view of a portion of the catheter of FIG. 14A taken along line 15-15. A wire assembly 101 is depicted that is attached to the catheter near the distal tip and extends proximally through lumen 102 towards the proximal end of the catheter. Lumen 105 extends from the proximal end of the catheter to the distal tip, configured for injection of contrast material into the biliary tree and to accept a guidewire. The embodiment eliminates one of the lumens to save space. Lumens 103 A and 103 B are two separate lumens for independent inflation and deflation of two separate balloons. These were not visible as separate lumens on side sectional view because of the limitations of a two-dimensional figure. These can be clearly appreciated as separate, parallel lumens on this cross-sectional view. The low-compliance, high-pressure dilator balloon on the distal shaft is filled under pressure with the infusion of fluid through lumen 103 B that extends proximally from the dilator balloon to the proximal end of the catheter. The low pressure, high compliance stone extraction/retrieval balloon located more distally on the shaft for It is filled independently through a separate lumen 103 A that extends proximally from the balloon to the proximal end of the catheter.

FIG. 16 depicts a cross-sectional view of a portion of the catheter of FIG. 14A taken along line 16-16. This cross-sectional view is distal to the dilator balloon and therefore lumen 103 B in not present. Otherwise, it is identical to FIG. 15.

FIG. 17 depicts a cross-sectional view of a portion of the catheter of FIG. 14A taken along line 17-17. This cross-sectional view is distal to the stone extraction/retrieval balloon and therefore lumen 103 A in not present. Otherwise, it is identical to FIG. 16.

FIG. 18 depicts a cross-sectional view of a portion of the catheter of FIG. 14 B taken along line 18-18. It is identical to FIG. 15.

FIG. 19A depicts a side sectional view of the distal part of the fourth embodiment of the catheter. The wire assembly 901 is in a needle-knife configuration. In this configuration the manipulation of the handle allows the tip of the electrosurgical wire to slide in and out to the distal tip of the catheter. This allows the catheter to cut into the bile duct directly when cannulation of the bile duct is not feasible because of difficult anatomy. The wire assembly 901 has a cutting (conductive) part at the distal tip that slides in and out of the tip of the catheter and a non-conductive part that extends proximally through lumen 902 towards the proximal end to be attached to a handle that controls the movement of the wire. Lumen 105 extends from the proximal end of the catheter to the distal tip, configured for injection of contrast material into the biliary tree and to accept a guidewire. The embodiment eliminates one of the lumens to save space. A Tuohy-Borst adapter may be built in or attached to the proximal end of the lumen to backflow of contrast. The catheter may be configured to be preloaded with a guidewire if desired. Lumens 103 A & B are two separate lumens for independent inflation and deflation of two separate balloons. These are not visible as separate lumens on side sectional view because of the limitations of a two-dimensional figure. These can be clearly appreciated as separate, parallel lumens on subsequent cross-sectional views. The catheter houses a low-compliance, high-pressure dilator balloon 109 on the distal shaft. This balloon is filled under pressure with the infusion a fluid through lumen 103 B that extends proximally from the balloon to the proximal end of the catheter. It has side holes 107 to allow the entry and exit of fluid from the lumen into the dilator balloon. It is filled under pressure with a fluid e.g., diluted contrast material, to expand the balloon to a predetermined diameter to dilate the ampulla of Vater. It may be configured to be inflated to a single diameter or several different diameters (multi-diameter) based on the pressure level achieved with the amount of the fluid administered (staged inflation). The catheter also houses a second low-pressure, high-compliance balloon 108 located more distally on the shaft for stone extraction/retrieval. It is filled independently through a separate lumen 103 A that extends proximally from the balloon to the proximal end of the catheter. It has side holes 106 to allow the entry and exit of air from the lumen into the extractor balloon. It can be configured to be inflated to one fixed or several different predetermined diameters based on the volume of air introduced. Radiopaque markers 110 may be placed to mark the proximal and distal ends of the dilator balloon for optimal positioning of the catheter under fluoroscopy. The catheter, however, can also be positioned at the ampullary orifice under visual endoscopic guidance. Additional fluoroscopic markers may be placed as desired, for example at the proximal end of the stone extractor balloon as desired. Color coded visual markers may be placed on the catheter at various locations as desired for guidance under endoscopic view.

FIG. 19 B depicts a side sectional view of the proximal part of the same embodiment of the catheter shown in FIG. 19A. Wire assembly 901 extends through lumen 902 to be attached to the handle 903 that controls the movements of the wire and the wire tip. The wire connects to a RF heating source through a RF connector 113. Lumen 103 B from the dilator balloon extends to the proximal end of the catheter and it has a luer lock or another compatible connector 114 at the proximal end to be attached to a pressure gauge and a 60-cc inflation device/fluid filled syringe (not shown). It is used to fill the dilator balloon under pressure with a fluid e.g., diluted contrast material, normal saline or sterile water, configured to inflate the balloon to one fixed diameter or several different predetermined diameters based on the pressure level achieved with the amount of the fluid administered. Lumen 103 A extends proximally from the stone extraction balloon to the proximal end of the catheter. It has a connector 115 at the proximal end to be attached to a syringe filled with air (not shown). The stone extraction balloon can be configured to be inflated to one fixed or several different predetermined diameters based on the volume of air introduced. Lumen 105 is the lumen with the largest diameter configured to accept a guidewire and contrast injection. A Tuohy-Borst adapter 116 may be built-in or attached to the proximal end of the lumen to prevent backflow of contrast. The silicone valve and cap 117 of the Tuohy-Borst adapter torque around the guidewire while contrast is injected through the injection port 118.

FIG. 20 depicts a cross-sectional view of a portion of the catheter of FIG. 19A taken along line 20-20. A wire assembly 901 is depicted that is attached to the catheter near the distal tip and extends proximally through lumen 902 towards the proximal end of the catheter. Lumen 105 extends from the proximal end of the catheter to the distal tip, configured for injection of contrast material into the biliary tree and to accept a guidewire. The embodiment eliminates one of the lumens to save space. Lumens 103 A and 103 B are two separate lumens for independent inflation and deflation of two separate balloons. These were not visible as separate lumens on side sectional view because of the limitations of a two-dimensional figure. These can be clearly appreciated as separate, parallel lumens on this cross-sectional view The low-compliance, high-pressure dilator balloon on the distal shaft is filled under pressure with the infusion of fluid through lumen 103 B that extends proximally from the dilator balloon to the proximal end of the catheter. The low pressure, high compliance stone extraction/retrieval balloon located more distally on the shaft for It is filled independently through a separate lumen 103 A that extends proximally from the balloon to the proximal end of the catheter.

FIG. 21 depicts a cross-sectional view of a portion of the catheter of FIG. 19A taken along line 21-21. This cross-sectional view is distal to the dilator balloon and therefore lumen 103 B in not present. Otherwise, it is identical to FIG. 20.

FIG. 22 depicts a cross-sectional view of a portion of the catheter of FIG. 19A taken along line 22-22. This cross-sectional view is distal to the stone extraction/retrieval balloon and therefore lumen 103 A in not present. Otherwise, it is identical to FIG. 21.

FIG. 23 depicts a cross-sectional view of a portion of the catheter of FIG. 19 B taken along line 23-23. It is identical to FIG. 20.

FIG. 24A depicts a side sectional view of the distal part of the first embodiment of the catheter demonstrating different ways a guidewire can be loaded. The guidewire may be loaded to extend through the entire length of the lumen 105, depicted by guidewire 2402, protruding from each end in a long-wire or short-wire configuration of the catheter as desired. Alternatively, and additionally a side-hole near the distal tip shown by dashed lines 111 can be used for guidewire acceptance as depicted by guidewire 2401, for the catheter to be used as an ultra-short wire system for intraductal exchange. A radiopaque marker may be placed at the level of the side hole to facilitate intraductal exchange. Multiple guidewires can be placed simultaneously without requiring a catheter exchange, to cannulate multiple ducts, place multiple stents or do other simultaneous interventions.

Figure 24:
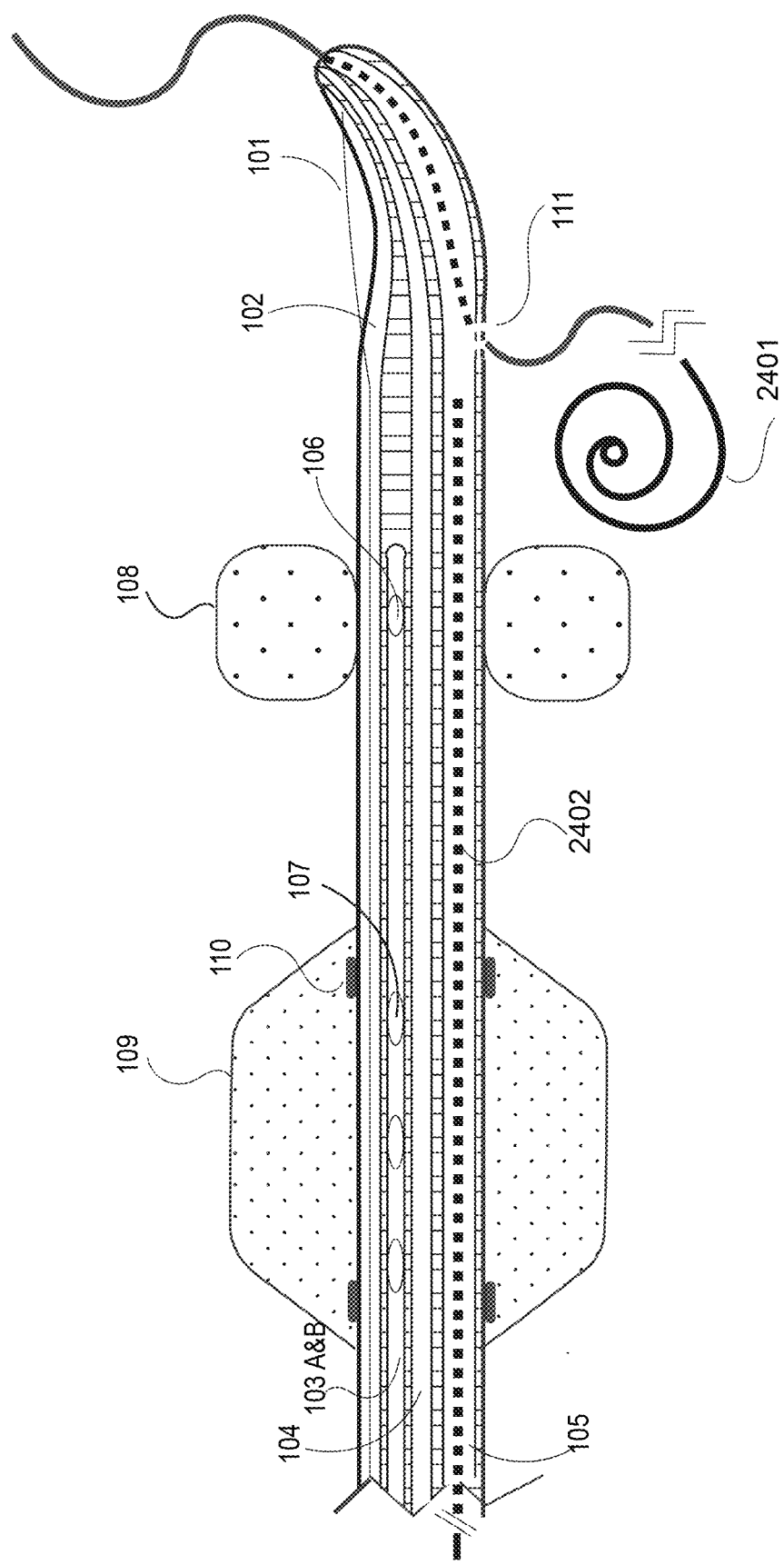
FIG. 24 B depicts a side sectional view of the proximal part of first embodiment demonstrating that the catheter can be used as a part of a long-wire or short-wire system.

FIG. 24 B depicts a side sectional view of the proximal part of first embodiment demonstrating that the catheter can be used as a part of a long-wire or short-wire system. If the catheter is configured as a long-wire catheter, guidewire 2403 would run through the entire length of the lumen 105 from the wire port 117 to the distal tip. Alternatively, it may have splitable channel in the form of C, U, 0 or other potential channels for use as a short-wire system, as depicted by the guidewire 2404 shown as being separated away from lumen 105. Furthermore, the catheter in either of these configurations, long-wire or short-wire, would have additional ultra-short wire capability as demonstrated in if FIG. 24A.

Figure 25:
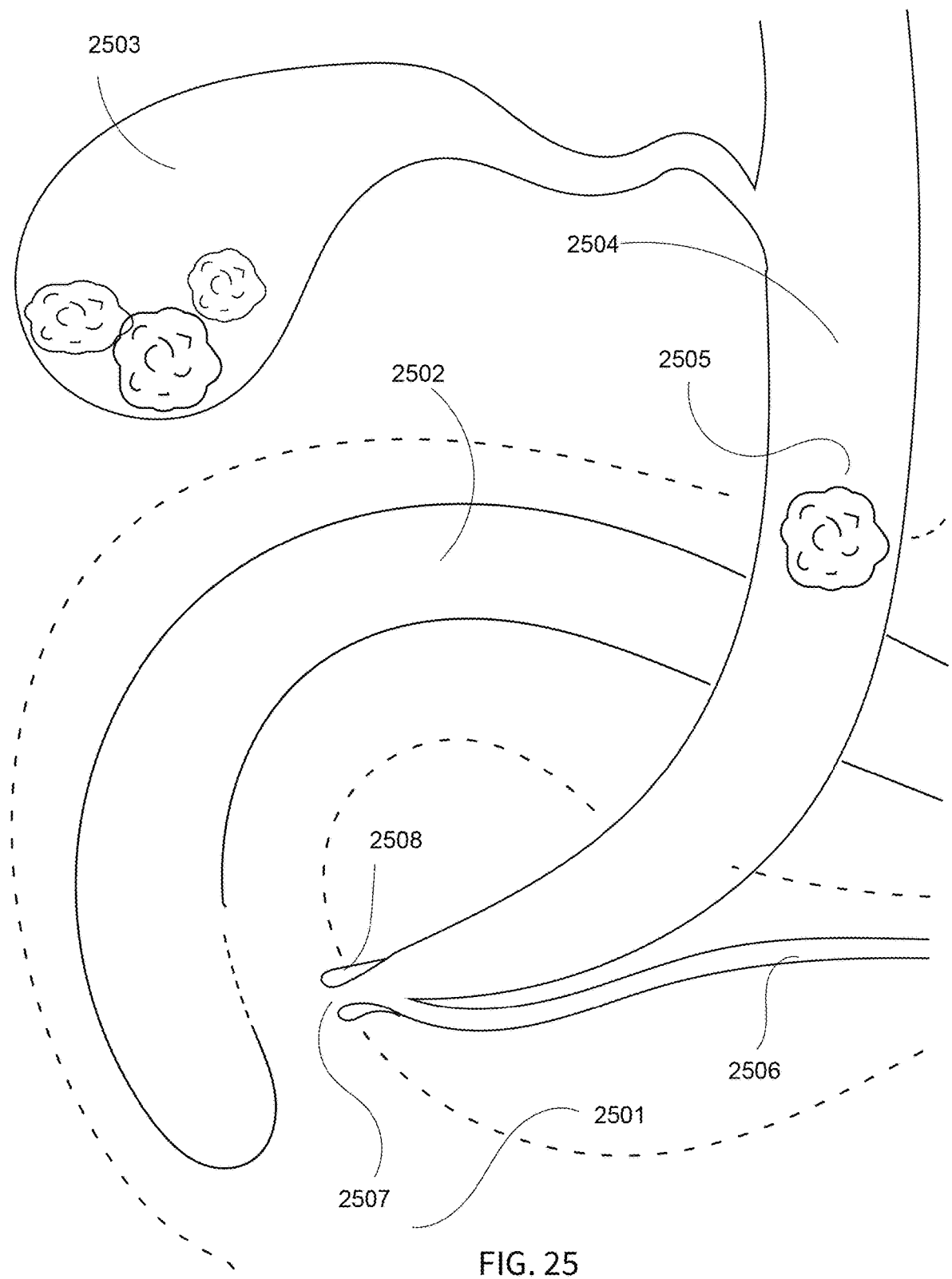
FIG. 25 demonstrates a view of a duodenoscope in position in the duodenum, a bile duct stone is noted in the bile duct.

FIG. 25 demonstrates a view of a duodenoscope 2502 in position in the duodenal lumen 2501 for an ERCP procedure. A bile duct stone 2505 is noted in the bile duct 2504. The pancreatic duct 2506 joins the bile duct at the ampullary orifice 2507, surrounded by the sphincter of Oddi 2508. Gallbladder 2503 containing stones is also seen.

Figure 26:
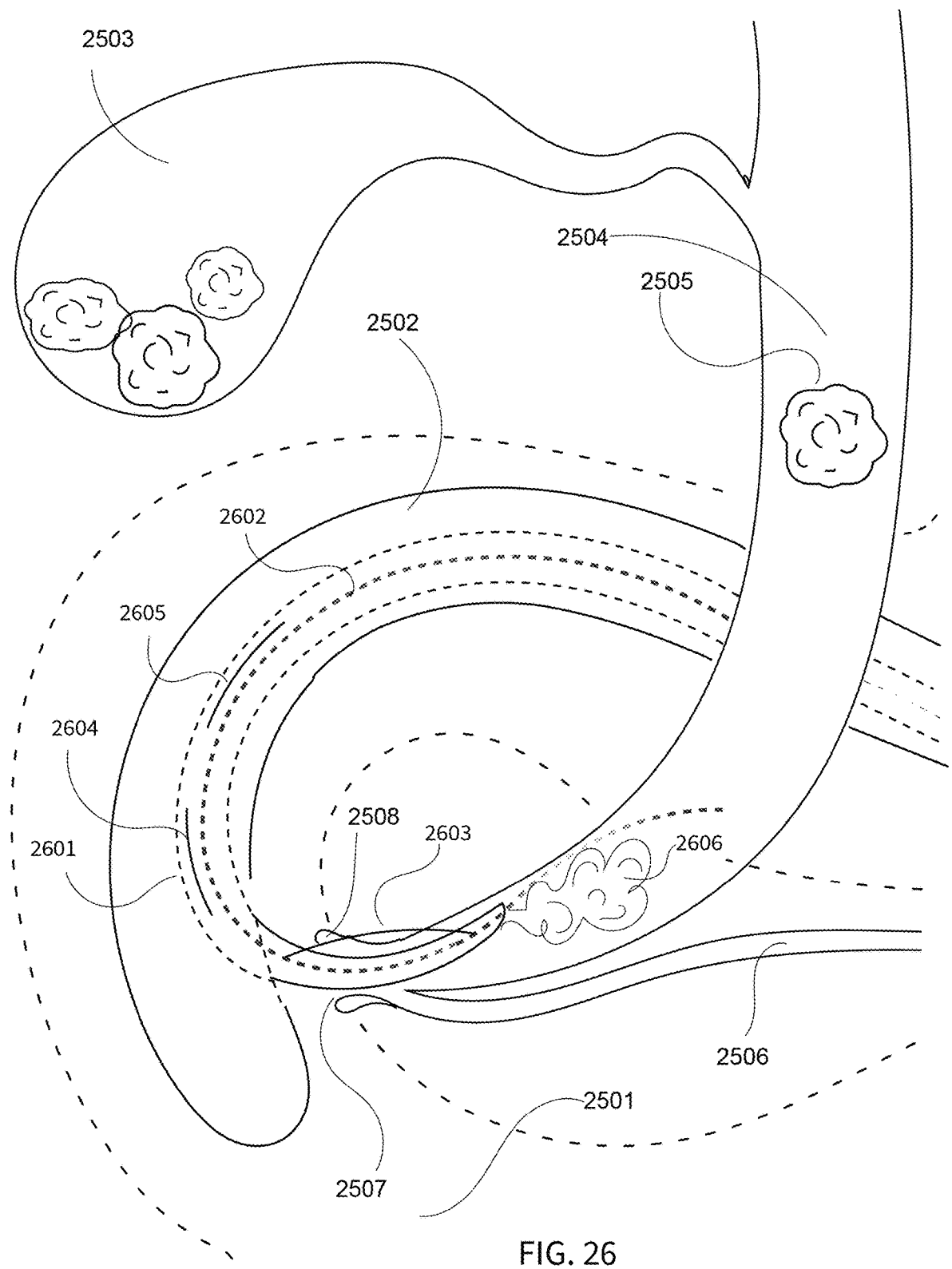
FIG. 26 demonstrates a view of the first embodiment of the catheter in action with the catheter tip engaged in the ampullary orifice and the sphincter of Oddi being cut by the cutting wire.

FIG. 26 demonstrates a view of the first embodiment of the catheter 2601 in action over a guidewire 2602 with the catheter tip engaged in the ampullary orifice 2507 and contrast 2606 has been injected. The sphincter of Oddi 2508 is being cut by the cutting wire 2603 of the catheter. The stone extraction/retrieval balloon 2604 and the dilator balloon 2605 are both in a deflated state within the working channel of the duodenoscope 2502.

Figure 27:
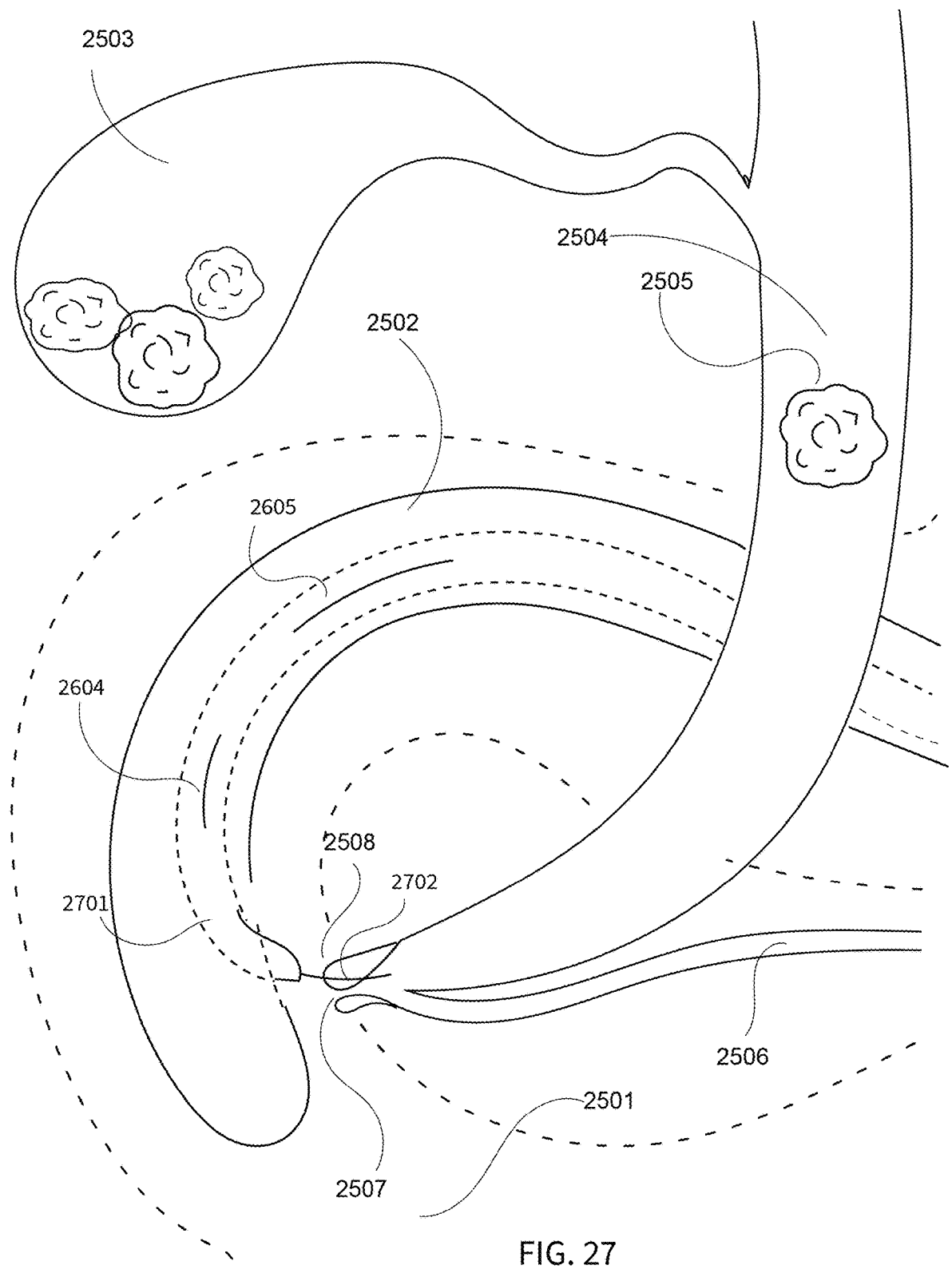
FIG. 27 demonstrates a view of the second embodiment of the catheter in action with a needle-knife being used to cut into the papilla to gain bile duct access.

FIG. 27 demonstrates a view of the second embodiment of the catheter 2701 in action with a needle-knife 2702 being used to cut into the sphincter of Oddi 2508 to gain access into the bile duct 2504. The stone extraction/retrieval balloon 2604 and the dilator balloon 2605 are both in a deflated state within the working channel of the duodenoscope 2502.

Figure 28:
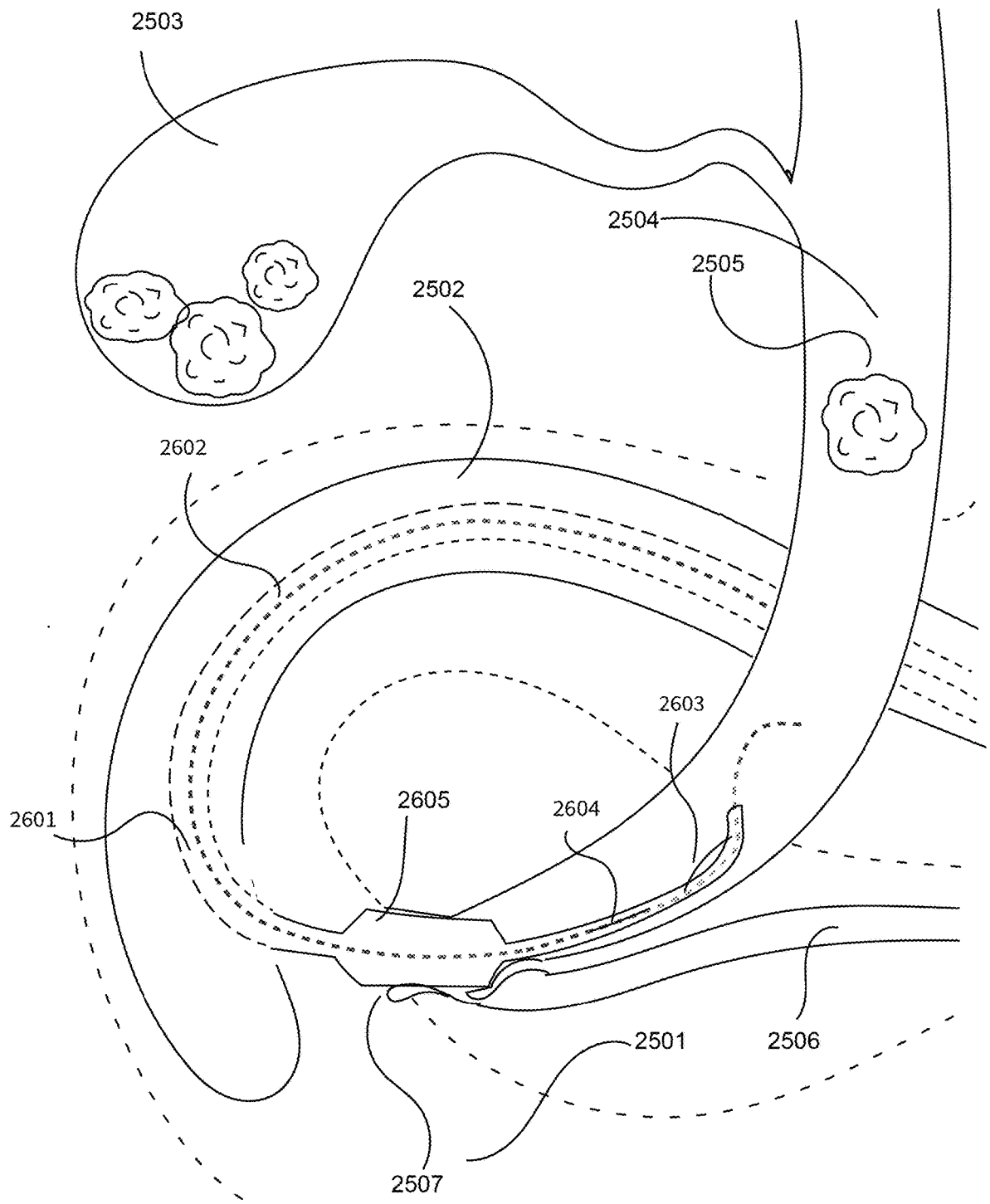
FIG. 28 demonstrates a view of the first embodiment of the catheter being introduced into the bile duct over a guidewire and the dilator balloon in position in the inflated state causing expansion of the ampullary orifice.

FIG. 28 demonstrates a view of the first embodiment of the catheter 2601 being introduced into the bile duct 2504 over a guidewire 2602. The dilator balloon 2605 is in position in the inflated state causing expansion of the ampullary orifice 2507. The stone retrieval balloon 2604 in the deflated state.

Figure 29:
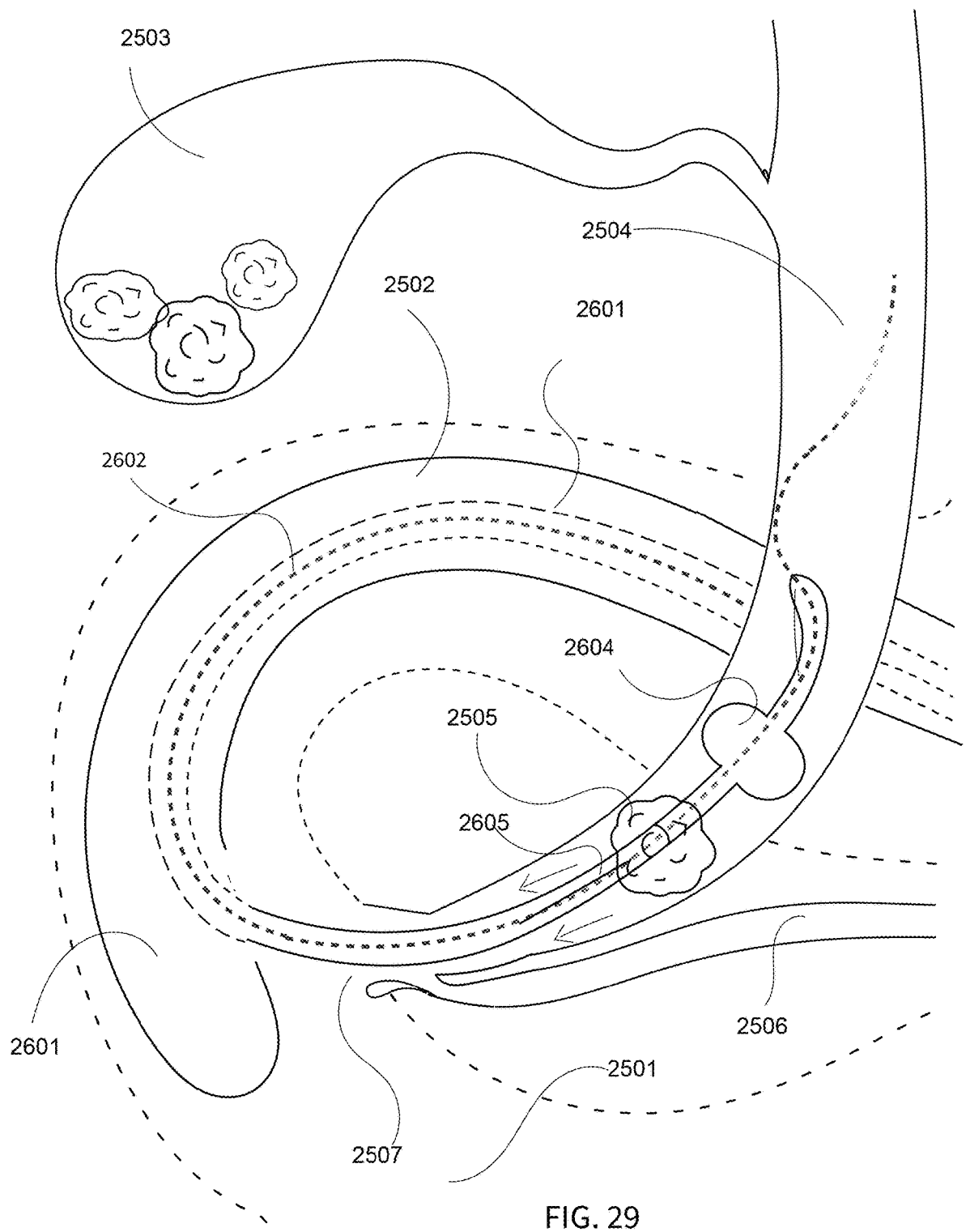
FIG. 29 demonstrates a view of the first embodiment of the catheter in the bile duct over a guidewire with the stone retrieval balloon in the inflated state positioned proximal to a bile duct stone, in the process of sweeping the stone out of the bile duct and into the duodenum.

FIG. 29 demonstrates a view of the first embodiment of the catheter 2601 in the bile duct 2504 over a guidewire 2602. The dilator balloon 2605 is in a deflated state. The stone extractor/retrieval balloon 2604 in the inflated state positioned proximal to a bile duct stone 2505, in the process of sweeping the stone out of the bile duct and into the duodenal lumen 2501.

Figure 30:
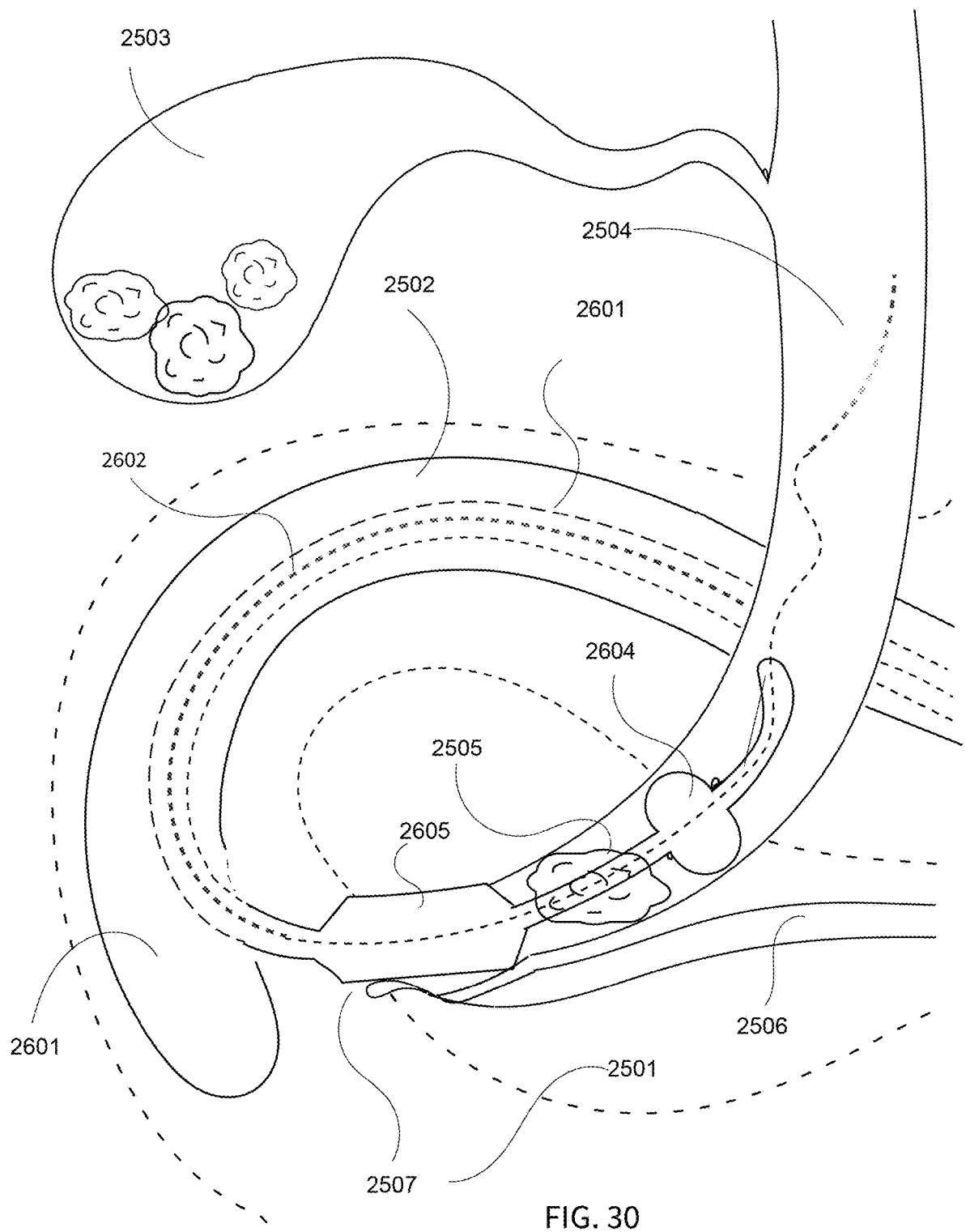
FIG. 30 demonstrates a view of the first embodiment of the catheter in the bile duct over a guidewire with the stone retrieval balloon in the inflated state positioned proximal to a bile duct stone while the dilator balloon is also in an inflated state. This may be a useful option to keep the biliary outflow tract straight and optimally aligned during the stone retrieval process. This can be particularly helpful in situations when the bile duct is sharply angulated, or the stone has sharp edges.

FIG. 30 demonstrates a view of the first embodiment of the catheter in the bile duct over a guidewire with the stone retrieval balloon in the inflated state positioned proximal to a bile duct stone while the dilator balloon is also in an inflated state. This may be a useful option to keep the biliary outflow tract straight and optimally aligned during the stone retrieval process. This can be particularly helpful in situations when the bile duct is sharply angulated, or the stone has sharp edges.

One of the lumens may have a large enough diameter to allow the passage of a 0.035 inch or a 0.025 inch guidewire. With improvements in guidewire materials, design and maneuverability, 0.025 inch guidewire has become more useful may become the new standard guidewire. It is possible that even a smaller diameter guidewire lumen may have utility in the future with further improvements in guidewire design. The other lumens can be quite small, and some of the lumens can be arranged along the periphery and/or have non-circular cross-sectional shapes to optimally utilize the space within the catheter. The locations, shapes and sizes of each lumen may be modified. It may be configured to a be part of long-wire system or it may have splitable channel in the form of C, U, O or other potential channels for use as a short-wire system. Additionally, it may have a side hole (side-port) near the distal tip for guidewire acceptance, approximately 2 to 8 cm from the distal tip, to be compatible with an ultra-short wire system for intraductal exchange. For use as a primary access device for an ultra-short wire exchange, the guidewire may be loaded through the distal side-port to exit from the tip for a comfortable distance and the two advanced together through the working channel of the duodenoscope. If it is difficult to keep the two coupled together through the working channel, the guidewire may be advanced first until it exits the tip of the duodenoscope. The guidewire can then be locked with the elevator and the catheter advanced over it until the two can be seen to be aligned at the tip of the duodenoscope under endoscopic view. After deep cannulation of the biliary tree, the catheter can be advanced and/or the guidewire can be pulled back to uncouple the two for intraductal exchange. The catheter can then be removed for a second device to be introduced over the guidewire. Additionally, or alternatively, a second guidewire may be introduced through the proximal end of the guidewire lumen while the catheter is still in place, if two guidewires are needed for a double-guidewire technique or for multiple stent/device placements. If for some reason, a different catheter was used to gain bile duct access and place a guidewire, this catheter can also be used as a secondary ultra-short wire device with the guidewire entering through the tip and exiting through the distal side-port. It may also be used as a secondary device for a short-wire or long-wire exchange.

The distal side-hole (side port) in the guidewire lumen (or an opening in another lumen) may configured to be used for injection of contrast or fluid to be strategically administered between two inflated balloons, or proximally or distally to one of the inflated balloons for selective contrast injection or for infusion of a medicine, chemical, biologic agent or a vector for gene therapy within the biliary tree or another lumen.

The catheter of this device may be constructed from any of a wide variety of suitable materials or blend of materials that are currently available such as nylon, teflon, silicone, polyurethane, polyethylene or polyvinyl chloride (PVC), or other materials that may become available in the future. The cutting wire may be constructed from any of the currently available materials like stainless steel, nitinol, tungsten or any materials that may become available in the future. The low-compliance, high-pressure dilator balloon may be constructed from PET (polyethylene terephthalate), nylon, Pebax or other similar materials or blend of materials that have high hoop strength to achieve high dilating forces. The low-pressure, high-compliance stone may be constructed from silicone, latex, polyurethane and other similar materials or blend of materials. Materials suitable for recycling may be used as much as possible. It is not the purpose of this document to provide specific measurements, however some general guidance may be appropriate. The length of the dilating balloon in the range of 2 to 4 cm may be optimal for dilation of the ampulla of Vater, other lengths are also acceptable. Catheters are generally constructed with multiple balloon diameter choices for the dilator balloons, whether single diameter or multidiameter (staged inflation), to match the diameter of the bile duct lumen. The stone extraction/retrieval balloons typically range in length from 1 cm to 3 cm. For a catheter with multiple elements, a length towards the shorter end of the range would be optimal. Catheters are generally constructed with multiple balloon diameter choices for stone extraction/retrieval balloons to match or exceed the diameter of the bile duct lumen. The exposed part of the cutting wire can vary in length from 1 cm to 3 cm, again a length towards the shorter end of the range would be desirable. The nose of the sphincterotome (the distance from the distal end of the exposed cutting wire to the distal tip of the catheter) typically ranges from 0.5 to 1.5 cm. For a catheter like this with multiple elements, a length in the lower end of the range would be optimal. The distance between the exposed part of the cutting wire and the extraction/retrieval balloon and between the extraction/retrieval balloon and the dilator balloon may be in the range of 1 cm to 2.5 cm, although other distances may be acceptable.

The biliary system is used as an example. The device, however, is not limited in its scope to use in the biliary system/gastroenterology applications and can be utilized in any human or non-human body lumen, cavity or organ for a variety of applications including but limited to interventional radiological, robotic surgical, urological, gynecological, cardiovascular and neurovascular procedures. It may be used with or without a guidewire. The term 'guidewire' used in this document would encompass not only the guidewire or wire guide in a traditional sense of the word but also include any elongate member that can perform a similar function e.g., a small diameter catheter, basket, stylet, needle, cable, string, laser fiber, EHL fiber, light source, fiberoptic or videoscope. The device maybe constructed using any of a variety of suitable materials that are currently available or may become available in the future. Although, the heat source for the cutting wire is typically radiofrequency (RF) electrical current, the term heat source would encompass any available source of heat or energy including but not limited to other forms of electric currents, laser, electrohydraulic, ultrasonic, gamma rays and microwaves.

What is claimed is:

1. A medical device configured for large stone extraction comprising:
    a flexible elongate catheter comprising a plurality of lumens, a proximal end and a distal end, a longitudinal axis extending from said proximal end to said distal end, an electrosurgical wire assembly that has a distal cutting part for performing a sphincterotomy and a non-conductive part that extends proximally through a first lumen towards the proximal end to be attached to a heat source and a handle that controls tip deflection/manipulation, wherein a distal tip of the catheter is curved towards the first lumen such that a distal end of the electrosurgical cutting wire is attached to the distal tip, and wherein the first lumen terminates proximal to the distal tip such that the cutting part is exposed within a recess defined by the curvature of the distal tip and the end of the first lumen;
    a second lumen extending from the distal end to the proximal end, configured to accept a contrast injection through the proximal end for cholangiography or similar uses;
    a third lumen extending from the distal end to the proximal end, configured to accept a guidewire, wherein the lumen may be constructed without a split for the catheter to operate as a long-wire catheter or alternatively may be configured to have a splitable channel in the form of a C, U, O configuration or other similar channels for use as a short-wire catheter;

a low-compliance, high-pressure dilator balloon located on the catheter towards the distal end, configured for dilation of an ampulla of Vater or a stricture, wherein the dilator balloon is filled via infusion of a fluid through a fourth lumen that extends proximally from one or more dilator balloon entry ports to the proximal end of the catheter, with a luer lock or another compatible connector at the proximal end to be attached to a pressure gauge and an inflation device, configured to be dilated to one fixed diameter or several different predetermined diameters dependent on the pressure level achieved;

a second low-pressure, high-compliance extractor balloon located distal of the dilator balloon on the catheter for extraction/retrieval of stones or other objects, wherein the extractor balloon is filled through a fifth lumen that extends proximally from one or more extractor balloon entry ports to the proximal end of the catheter with a connector for a syringe, configured to be inflated to one fixed or several different predetermined diameters based on a volume of air introduced through a syringe;

an additional side-hole, optionally incorporated near the distal end of the third lumen for the catheter to have additional guidewire exchange capability as an ultra-short wire exchange catheter; and one or more radiopaque markers, optionally incorporated to mark certain areas of the catheter, with or without color coded visual markers at various locations as desired.

2. A medical device configured for large stone extraction comprising:

a flexible elongate catheter comprising a plurality of lumens, a proximal end and a distal end, a longitudinal axis extending from said proximal end to said distal end, an electrosurgical wire assembly that has a distal cutting part for performing a sphincterotomy and a non-conductive part that extends proximally through a first lumen towards the proximal end to be attached to a heat source and a handle that controls tip deflection/tip manipulation, wherein a distal tip of the catheter is curved towards the first lumen, such that a distal end of the electrosurgical cutting wire is attached to the distal tip, and wherein the first lumen terminates proximal to the distal tip such that the cutting part is exposed within a recess defined by the curvature of the distal tip and the end of the first lumen;

a second lumen extending from the distal end to the proximal end, configured to accept a contrast injection through the proximal end for cholangiography or similar uses and also configured to accept a guidewire, with a Tuohy-Borst adapter that may be built in or attached to the proximal end;

a low-compliance, high-pressure dilator balloon located on the catheter towards the distal end, configured for dilation of an ampulla of Vater or a stricture, wherein the dilator balloon is filled via infusion of a fluid through a third lumen that extends proximally from one or more dilator balloon entry ports to the proximal end of the catheter, with a luer lock or another compatible connector at the proximal end to be attached to a pressure gauge and an inflation device, configured to be dilated to one fixed diameter or several different predetermined diameters dependent on the pressure level achieved;

a second low-pressure, high-compliance extractor balloon located distal of the dilator balloon on the catheter for extraction/retrieval of stones or other objects, wherein the extractor balloon is filled through a fourth lumen that extends proximally from one or more extractor balloon entry ports to the proximal end of the catheter with a connector for a syringe, configured to be inflated to one fixed or several different predetermined diameters based on a volume of air introduced through a syringe;

an additional side-hole, optionally incorporated near the distal end of the second lumen for the catheter to have additional guidewire exchange capability as an ultra-short wire exchange catheter; and one or more radiopaque markers, optionally incorporated to mark certain areas of the catheter, with or without color coded visual markers at various locations as desired.

3. A method of using a medical device described in claim 1, comprising the steps of:

introducing the medical device through a duodenoscope or another videoscope, port, sheath or opening in order to streamline bile duct stone extraction by eliminating the need for multiple catheter exchanges in an attempt to improve efficiency, ensure patient safety, reduce healthcare costs and minimize medical waste;

cutting a biliary sphincter with said electrosurgical cutting wire;

dilating a biliary orifice with said low-compliance, high-pressure dilator balloon; and extracting bile duct stones or other objects from the biliary tree with the use of said low-pressure, high-compliance extractor balloon, without requiring any catheter exchanges, as all three components are housed within one catheter.

* * * * *